United States Patent
Giritch et al.

(10) Patent No.: US 9,856,484 B2
(45) Date of Patent: *Jan. 2, 2018

(54) PLANT TRANSFORMATION WITH IN VIVO ASSEMBLY OF A TRAIT

(75) Inventors: Anatoly Giritch, Halle/Saale (DE); Sylvestre Marillonnet, Halle/Saale (DE); Victor Klimyuk, Halle/Saale (DE); Yuri Gleba, Halle/Saale (DE)

(73) Assignee: BAYER CROPSCIENCE N.V., Diegem (BE)

( * ) Notice: Subject to any disclaimer, the term of this patent is extended or adjusted under 35 U.S.C. 154(b) by 1225 days.

This patent is subject to a terminal disclaimer.

(21) Appl. No.: 10/545,665

(22) PCT Filed: Jan. 30, 2004

(86) PCT No.: PCT/EP2004/000891
§ 371 (c)(1),
(2), (4) Date: Oct. 13, 2005

(87) PCT Pub. No.: WO2004/067748
PCT Pub. Date: Aug. 12, 2004

(65) Prior Publication Data
US 2007/0124831 A1 May 31, 2007

(30) Foreign Application Priority Data

Jan. 31, 2003 (DE) .................................. 103 03 937
Jul. 17, 2003 (DE) .................................. 103 32 597

(51) Int. Cl.
C12N 15/82 (2006.01)

(52) U.S. Cl.
CPC ................................ C12N 15/8205 (2013.01)

(58) Field of Classification Search
None
See application file for complete search history.

(56) References Cited

U.S. PATENT DOCUMENTS

| | | | |
|---|---|---|---|
| 5,501,967 A | 3/1996 | Offringa et al. | |
| 6,376,745 B1 | 4/2002 | Atabekov et al. | |
| 6,413,777 B1 | 7/2002 | Reff et al. | |
| 6,531,316 B1 * | 3/2003 | Lassner et al. | 435/455 |
| 6,566,584 B1 * | 5/2003 | Coughlan | 800/281 |
| 6,632,980 B1 | 10/2003 | Yadav et al. | |
| 7,112,721 B2 | 9/2006 | Fabijanski et al. | |
| 7,267,979 B2 * | 9/2007 | Yadav | 435/320.1 |
| 2005/0066384 A1 | 3/2005 | Klimyuk et al. | |

FOREIGN PATENT DOCUMENTS

| | | |
|---|---|---|
| WO | WO 99/55851 A2 | 11/1999 |
| WO | WO 02/081711 A1 | 10/2002 |
| WO | WO 02/088369 A1 | 11/2002 |
| WO | WO 02/097080 A2 | 12/2002 |

OTHER PUBLICATIONS

Deshpande et al. 1995, Current Genetics 28:122-127.*
Smith et al 2000, Nature, 407:319-320).*
Neve et al. 1997, The Plant Journal 11:15-29.*
De Block et al, 1991, Theor. Appl. Genet., 82:257-263.*
Smith et al, 2000, Nature, 407:319-320.*
Bilang, R., et al., "Single-Stranded DNA as a Recombination Substrate in Plants as Assessed by Stable and Transient Recombination Assays," *Molecular and Cellular Biology*, 1992, pp. 329-336, vol. 12, No. 1, American Society for Microbiology.
DeBuck, S., et al., "The DNA Sequences of T-DNA Junctions Suggest that Complex T-DNA Loci are Formed by a Recombination Process Resembling T-DNA Integration," *The Plant Journal*, 1999, pp. 295-304, vol. 20, No. 1, Blackwell Science Ltd., Great Britain.
DeNeve, M., et al., "T-DNA Integration Patterns in Co-Transformed Plant Cells Suggest that T-DNA Repeats Originate from Co-Integration Separate T-DNAs," *The Plant Journal*, 1997, pp. 15-29, vol. 11, No. 1, Oxford Publications, Great Britain.
Komari, T., et al., "Vectors Carrying Two Separate T-DNAs for Co-Transformation of Higher Plants Mediated by *Agrobacterium tumefaciens* and Segregation of Transformants Free from Selection Markers," *The Plant Journal*, 1996, pp. 165-174, vol. 10, No. 1, Blackwell Scientific Publications, Great Britain.
Krizkova, L., and M. Hrouda, "Direct Repeats of T-DNA Integrated in Tobacco Chromosome: Characterization of Junction Regions," *The Plant Journal*, 1998, pp. 673-680, vol. 16, No. 6.
Paszkowski, J., et al., "Expression in Transgenic Tobacco of the Bacterial Neomycin Phosphotransferase Gene Modified by Intron Insertions of Various Sizes," *Plant Molecular Biology*, 1992, pp. 825-836, vol. 19, Kluwer Academic Publishers, Belgium.
Zhao, X., et al., "T-DNA Recombination and Replication in Maize Cells," *The Plant Journal*, 2003, pp. 149-159, vol. 33, Blackwell Publishing Ltd.
Hoa, T.T.C. et al., "Cre/lox site-specific recombination controls the excision of a transgene from the rice genome," *Theor Appl Genet*, (2002) vol. 104, pp. 518-525.
De Groot, M., et al., "Mechanisms of intermolecular homologous recombination in plants as studied with single- and double-stranded DNA," *Nucleic Acids Research*, 1992, pp. 2785-2794, vol. 20(11).

(Continued)

*Primary Examiner* — Jason Deveau Rosen

(74) *Attorney, Agent, or Firm* — Williams Mullen, PC; David M. Saravitz

(57) ABSTRACT

A process of endowing a plant or plant cells with a trait of interest by expressing an RNA sequence of interest, said process comprising: providing plant cells or cells of said plant with a first vector and a second vector and selecting cells endowed with said trait of interest, wherein said first vector contains a first nucleotide sequence with a first segment coding, in 5' to 3' direction, for—a 5' part of said RNA sequence of interest and—a 5' part of an intron; and said second vector contains a second nucleotide sequence with a second segment coding, in 5' to 3' direction, for—a 3' part of an intron and—a 3' part of said RNA sequence of interest.

18 Claims, 15 Drawing Sheets

(56) References Cited

OTHER PUBLICATIONS

Offringa, R., et al., "Extrachromosomal homologous recombination and gene targeting in plant cells after *Agrobacterium* mediated transformation," *The EMBO Journal*, 1990, pp. 3077-3084, vol. 9(10).

Köhler et al., "Trans-splicing Ribozymes for Targeted Gene Delivery," *J. Mol. Biol.*, 1999, vol. 285, pp. 1935-1950.

Lewin, Benjamin, Chapter 33 "Recombination of DNA," *Genes V*, 1994, p. 967, Oxford University Press, Walton Street, Oxford OX26DP.

* cited by examiner

US 9,856,484 B2

PLANT TRANSFORMATION WITH IN VIVO ASSEMBLY OF A TRAIT

CROSS-REFERENCE TO RELATED APPLICATIONS

This application is the U.S. National Stage of International Application PCT/EP2004/000891, filed Jan. 30, 2004, which published in English on Aug. 12, 2004 and designates the U.S., and which claims the benefit of German Patent Application No. 103 03 937.6 filed Jan. 31, 2003 and German Patent Application No. 103 32 597.2 filed Jul. 17, 2003; all of which are hereby incorporated herein in their entirety by reference.

FIELD OF THE INVENTION

The present invention relates to a process of endowing a plant or plant cells with a trait of interest. Further the invention relates to a process of screening nucleotide sequences for a desired phenotype in plants. The invention also relates to transgenic plants and to libraries of plants or plant seeds obtained or obtainable according to the processes of the invention. Further, the invention relates to vectors for these processes and to plants or plant cells transformed therewith.

BACKGROUND OF THE INVENTION

Currently used methods of stable plant transformation usually employ direct (microprojectile bombardment, electroporation or PEG-mediated treatment of protoplasts, for review see: Gelvin, S. B., 1998, Curr. Opin. Biotechnol., 9, 227-232; Hansen & Wright, 1999, Trends Plant Sci., 4, 226-231) or Agrobacterium-mediated delivery of pre-engineered DNA vectors of interest into plant cells. Manipulations with said DNA vectors in planta are restricted to simplifying the resolution of complex integration patterns (U.S. Pat. No. 6,114,600; Srivastava & Ow, 2001, Plant Mol Biol., 46, 561-566; Srivastava et al., 1999, Proc. Natl. Acad. Sci. USA, 96, 11117-11121) or removal of auxiliary DNA sequences from vectors stably integrated into chromosomal DNA. The methods of stable Agrobacterium-mediated integration of T-DNA regions within plant cells use a desired DNA sequence to be integrated flanked with left (LB) and right (RB) border sequences necessary for T-DNA transfer and integration into the host chromosomal DNA (U.S. Pat. Nos. 4,940,838; 5,464,763; EP0224287; U.S. Pat. Nos. 6,051,757; 5,731,179; WO9400977; EP0672752). In most cases the approaches are directed to integration of one specific T-DNA region into the chromosomal DNA, less frequently the approaches are designed for co-integration of two or more different T-DNA regions (U.S. Pat. No. 4,658, 082). The latter approach is used for segregating different T-DNAs in progeny for various purposes. For example, Komari and colleagues (U.S. Pat. No. 5,731,179) describe a method of simultaneously transforming plant cells with two T-DNAs, one carrying a selectable marker functional in plants, while another T-DNA contains a desired DNA sequence to be introduced into plant cells. This allows to segregate in progeny transgenic plants without selectable marker.

The integration of a gene of interest into chromosomal DNA for expressing said gene can also be performed with the help of vectors that do not contain functional transcriptional promoters, but translation regulatory elements (WO0246440) called IRESs (internal ribosomal entry sites). Such vectors can provide for the expression of the gene of interest upon integration into the transcriptionally active region of chromosomal DNA. Another approach to provide for the expression of a promoterless gene or gene with minimal promoter also depends on integration into transcriptionally active regions (Stangeland et al., 2003, J. Exp. Bot., 54, 279-290; Baxter-Burrell et al., 2003, Ann. Bot. (Lond), 91, 129-141) or in close proximity to strong transcriptional enhancers (Baxter-Burrell et al., 2003, Ann. Bot. (Lond), 91, 129-141).

In general, the DNA regions designed for stable integration into plant cells are pre-engineered in vitro by employing standard molecular biology techniques (Sambrook, Fritsch & Maniatis, 1989, Molecular cloning: A laboratory manual, 2nd ed. Cold Spring Harbor, N.Y.: CSH Laboratory Press). Also, in vivo engineering in bacterial cells is used, for example in order to assemble a binary vector with the help of homologous recombination (U.S. Pat. No. 5,731,179). Manipulations with T-DNA in planta are restricted to T-DNA regions pre-integrated into a chromosome. Such manipulations were done for removing certain sequences from T-DNA, e.g. sequences encoding selectable markers including morphological abnormality induction genes. The removal of unwanted DNA fragments from T-DNA regions was tried either with the help of site-specific recombination (WO9742334; Endo et al., 2002, Plant J., 30, 115-122) or by means of transposition (U.S. Pat. No. 5,792,924). Although site-specific recombinase/integrase-mediated DNA excision is more efficient than integration, the selection for excision events is a necessity, which leads to yet an additional step of tissue culture or screening of progeny for desired recombination events. In summary, all processes of manipulation with T-DNAs stably integrated into plant chromosomes are time-consuming, inflexible, and in general restricted to simple excision (with less efficiency—to integration) of desired DNA fragments. In addition, these processes are usually very limited in combinatorial diversity, as they are restricted to simple manipulations with a limited number of known genes and regulatory elements.

Frequently, T-DNA regions co-integrate into the same locus (Jorgensen et al., 1987, Mol. Gen. Genet., 207, 471-477; Castle et al., 1993, Mol. Gen. Genet., 241, 504-514; Cluster et al, 1996, Plant Mol. Biol., 32, 1197-1203; DeNeve et al., 1997, Plant J., 11, 15-29) forming multimers of T-DNA regions. However, such complex integration events are usually undesired in any respect, as such complex arrangements are accompanied by the inactivation of the transgene (Cluster et al., 1996, Plant Mol. Biol, 32, 1197-1203; Jorgensen et al., 1996, Plant Mol. Biol., 31, 957-973). Transformation of plants with two different T-DNA regions, one carrying a coding sequence of a transformation marker, was used for generating transformation marker-free transgenic plants (Komari et al., 1996, Plant J., 10, 165-174). Co-integration of two copies of T-DNAs, one carrying a promoter and another carrying a promoterless neomycin phosphotransferase gene, was used to study the T-DNA cointegration pattern (Krizkova & Hrouda, 1998, Plant J., 16, 673-680).

The methods described above suffer from various shortcomings. In the method of Krizkova & Hrouda, one does not select for cointegration of both vectors (or both copies of the same vector). Instead, expressible transformation of the neomycin phosphotransferase gene is selected for, which may be due to fortuitous insertion of the promoterless neomycin phosphotransferase gene in a transcriptionally active chromosome region. Further, in methods using a single transformation vector, complex and time-consuming cloning procedures are required e.g. if the plant cells are to be transformed with a complex combination of sequences of interest (e.g. more than one gene to be expressed together with specific elements like recombination sites, regulatory sequences, transposon sequences etc.). Moreover, the above methods are not suited for methods of in vivo engineering like gene (or protein domain) shuffling or directed evolution. Furthermore, the above methods do not allow to obtain biologically safe transgenic plants, whereby the transgene of said transgenic plants is lost or rendered disfunctional in progeny of said transgenic plants.

Therefore, it is an object of the invention to provide an efficient, rapid and highly versatile process of producing a transgenic plant or transgenic plant cells. It is another object of the invention to provide a method of selecting for co-integration of two or more vectors transformed in plant cells. It is another object of the invention to provide a process of producing transgenic plants transformed on a chromosome, whereby the DNA sequences of interest are to be engineered in planta (e.g. for reducing cloning work or for transforming a DNA sequence of interest having toxic effects on bacteria that used for cloning). It is another object of the invention to provide a process of stable genetic transformation of plant cells, which allows the production of a library of traits or functions and/or screening for a desired trait (or function) from a library of traits (or functions). It is a further object of the invention to provide a process of producing environmentally safe transgenic plants, that transfer the transgenic function or trait to progeny with a low likelihood.

GENERAL DESCRIPTION OF THE INVENTION

The above objects are achieved by a process of endowing a plant or plant cells with a trait of interest by expressing an RNA sequence of interest, said process comprising:
providing plant cells or cells of said plant with a first vector and a second vector and selecting cells endowed with said trait of interest, wherein
said first vector contains a first nucleotide sequence with a first segment coding, in 5' to 3' direction, for
   a 5' part of said RNA sequence of interest and
   a 5' part of an intron; and
said second vector contains a second nucleotide sequence with a second segment coding, in 5' to 3' direction, for
   a 3' part of an intron and
   a 3' part of said RNA sequence of interest.

The invention further provides plants cells, plants or parts thereof like seeds that are endowed with a trait of interest according to the above process. Further, a library of plants or of plant seeds is provided. Preferably, the members of said library are endowed with different traits of interest. Moreover, a kit of parts is provided comprising said first and said second vector of the invention. Preferably, said first and/or said second vector of said kit-of-parts does not contain a site-specific recombination site for preventing site specific recombination between said first and said second vector.

This invention is based on the surprising finding that efficient assembly of transcribed sequences, notably of a coding sequence that encodes or results in a trait of interest, can be achieved by transforming plant cells with two or more vectors each carrying a segment coding for a part of a transcribed sequence or a part of said coding sequence. Providing, notably co-transforming, plant cells with said first and said second vector results with a high probability in integration of said vectors in proximity to each other in a chromosome of said plant cells.

Thereby, a functional transcription unit comprising sequences from both (different) vectors can be formed in said chromosome and selected for. Suitable positioning of 5' and 3' parts of an intron enables processing by intron splicing of a primary transcript derived from said transcription unit, whereby said RNA sequence of interest is formed. It was surprising to find the high efficiency with which plant cells or plants endowed with a trait of interest can be obtained by the process of the invention, not only if said first and said second vector are integrated in a chromosome contiguously but also if host chromosomal sequences separate the integrated vector sequences. Said efficiency is comparable to that for a standard *Agrobacterium*-mediated transformation with a single vector. The most surprising finding was the ability of co-integrated vector sequences (notably T-DNAs) to express a protein of interest (as a trait of interest) in said plant cells, when the sequence coding for said protein of interest is split in parts and each part is provided to said cells with a different vector.

The process of the invention allows to produce transgenic plants or plant cells that are stably transformed on a chromosome with sequences that derive at least from a first and a second vector. Stable transformation of a chromosome means integration in said chromosome such that said DNA sequence of interest is replicated together with said chromosome. Preferably, said DNA sequence of interest can be inherited during cell division and organism reproduction for several generations.

In the process of the invention, a plant or plant cells are endowed with a trait of interest. Examples for a trait of interest include expression of a protein of interest (e.g. a selectable marker, a protein that confers resistance e.g. against insects, pesticides, herbicides, heat, or a protein to be produced for industrial or pharmaceutical purposes) or down-regulation of a native gene of the host cells e.g. by RNA interference. Said trait of interest requires expression of said RNA sequence of interest. Translation of said RNA sequence of interest may lead to expression of a protein of interest, whereby said 5' part of said RNA sequence of interest may code for the N-terminal part of said protein of interest, and said 3' part of said RNA sequence of interest may code for the C-terminal part of said protein of interest. Further, said 5' or said 3' part of said RNA sequence of interest may be or may contain a regulatory element for translating a part of said RNA sequence of interest to a protein of interest. Alternatively, said RNA sequence of interest may cause said down-regulation of a native gene of the host cells.

Said first vector contains a first nucleotide sequence with a first segment coding, in 5' to 3' direction, for a 5' part of said RNA sequence of interest and a 5' part of an intron. Said second vector contains a second nucleotide sequence with a second segment coding, in 5' to 3' direction, for a 3' part of an intron and a 3' part of said RNA sequence of interest. Said first and said second nucleotide sequence are introduced into said plant cells by said first and said second vector. Said first and said second nucleotide sequence are adapted such that said plants or said cells can preferably be endowed with said trait of interest if and only if said plant cells are provided with said first vector and said second vector. Said RNA sequence of interest preferably cannot be expressed and said plant cells cannot be endowed with said trait of interest, if said plant cells or said plant is provided with only said first vector or only with said second vector. However, the process of the invention may be carried out such that a third vector (or further vectors) is additionally required for expressing said RNA sequence of interest (cf. FIG. 1 II).

According to the invention, said vectors have a high likelihood of forming a transcription unit comprising said first and said second nucleotide sequence. Such a transcription unit may be formed by co-integration of said vectors in a transcriptionally active region of a chromosome. Preferably, however, a transcription promoter is included in said first nucleotide sequence upstream of said first segment.

In the first step of the process of the invention, plant cells or a plant are provided at least with said first and said second vector. Plant cells may be provided with said at least two different vectors in tissue culture, notably in tissue of leaf pieces or in tissue culture of plant cell protoplasts. Further, explants (e.g. root explants, leaf discs) of a plant may be provided with said first and said second vector. Moreover, entire plants or parts of entire plants may be provided with said vectors. Preferably, said first vector and said second vector are provided such that they are integrated in a chromosome of said plant cells. Said chromosome may be a nuclear or an organellar (plastid or mitochondrial) chromosome. Preferably, said first and said second vector are integrated in a nuclear chromosome. In any case, said vectors should integrate in the same chromosome, notably the same nuclear chromosome, which may be achieved by suitable selection as described below.

Said vectors may be provided to said plant cells by any known transformation method, examples for which are particle bombardment, electroporation and *agrobacterium*-mediated transformation. However, in order to achieve a high likelihood of integration of said first and said second vector in proximity in said chromosome, it is highly preferred to provide said vectors by *Agrobacterium*-mediated transformation. In this case, said first and said second vector may be derived from a Ti-plasmid and said first and said second nucleotide sequence will each reside between T-DNA left border and right border sequences. Said left border and right border sequences may then provide for integration of said T-DNAs into said chromosome. Said first and said second vector may be provided to said cells consecutively. However, the efficiency of the process decreases with increasing time between providing said vectors. Preferably, said plant or said plant cells are therefore provided with said first and said second vectors in a one-step procedure, i.e. by co-transformation. In the case of direct vector delivery, this means that mixtures of said vectors are preferably used. In the case of *Agrobacterium*-mediated T-DNA delivery, mixtures of *Agrobacterium* strains (or cells) may be used, whereby each strain or cell should contain a different Ti-plasmid with either said first or said second vector (and optionally a third vector). Providing said plant cells or plants in a one step procedure with said vectors, notably simultaneously, is work-efficient and gives a good overall efficiency of the process of the invention.

Selecting plant cells endowed with said trait of interest may be done according to generally known methods. The selection method generally depends on the transformation method. Said first or said second nucleotide sequence may contain a selectable marker. Preferably, said trait of interest is resistance against a selective agent, allowing selection of transformed cells wherein the process of the invention has successfully occurred.

In the process of the invention, transcribed sequences encoded by different vectors may be brought together in said RNA sequence of interest for producing said trait of interest. Examples of such transcribed sequences are sequences coding for a protein of interest and sequences involved in regulation of translation (like an IRES element, a 5' untranslated sequence or a 3' untranslated region), and an RNA sequence for RNA interference. Promoters are not transcribed sequences. In a basic embodiment, the process of the invention comprises translation of said RNA sequence of interest to produce a protein of interest. Said trait of interest may be due to said protein of interest. In this case, said protein of interest can preferably be expressed only if said plant cells are provided with said first and said second vector, which can be achieved in several ways. Said first segment or said second segment may e.g. code for a translation regulatory element (like an internal ribosome entry site IRES, or a 5'- or a 3'-untranslated region) and the other segment may code for said protein of interest. Preferably, however, said first segment encodes a 5' part of said protein of interest and said second segment encodes a 3' part of said protein of interest, preferably such that said trait of interest is produced only if said first and said second vector are provided to said plant cells or said plant. One or both of said segments may further contain a translation regulatory element or other non-translated sequences.

If said trait of interest is due to a protein of interest, said RNA of interest can be translated in said cells to express said protein of interest. Expression of said protein of interest proves that said RNA sequence of interest has been expressed. Expression of the protein of interest requires intron splicing of a primary transcript to form said RNA sequence of interest by way of said 5' and said 3' part of an intron. Said intron parts should be adapted such that splicing of the primary transcript leads to an RNA sequence of interest with the correct reading frame for expression of a functional protein of interest. For this purpose, said 5' part of said RNA sequence of interest is preferably contiguous to the 5' part of an intron and said 3' part of an intron is preferably contiguous to the 3' part of said RNA sequence of interest.

Said 5' part of an intron and said 3' part of an intron is encoded by said first and said second segment, respectively. The sequences coding for the intron parts may be taken from a known intron. Said intron may be a self-splicing intron, e.g. a group I or a group II intron. Alternatively, said intron may be an intron of a nuclear pre-mRNA for spliceosome-mediated splicing. Introns of a nuclear pre-mRNA for splicesome-mediated splicing are most preferred. A DNA sequence encoding an intron may be split into sequences encoding said 5' and said 3' intron parts and incorporated into said first and said second segment, respectively. Said splitting has to be such that said 5' and said 3' intron parts are functional as an intron, which may be tested experimentally. A naturally occurring intron may be modified provided said intron parts stay functional as an intron. Sequences encoding said intron parts may of course also be synthesized artificially and incorporated in said first and second segments (see examples).

A basic embodiment of the invention is exemplified in FIG. 10 and FIG. 11. According to FIG. 10, said first vector contains a first nucleotide sequence (shown in A) with a first segment coding for the 5' part of a selectable marker and the 5' part of an intron. Said second vector contains a second nucleotide sequence (shown in B) with a second segment coding for the 3' part of an intron and the 3' part of a selectable marker. Application of a selective agent to cells transformed with said first and said second vector allows selecting for such a mode of co-integration, wherein said vectors form a functional transcription unit (depicted in C). A primary transcript produced in plant cells under the control of a promoter upstream of said first segment leads to a primary transcript comprising, in 5' to 3' direction, the 5' part of said selectable marker, the 5' part of said intron, possibly sequences deriving from the host chromosome, the 3' part of said intron, and the 3' part of said selectable marker. Said intron parts allow intron splicing of said primary transcript to form said RNA sequence of interest. Translation of said RNA sequence of interest endows said cells with a resistance to said selective agent as a trait of interest. As shown in FIG. 11, the selectable marker may be any other gene of interest. According to general knowledge, said 5' part of an intron and said 3' part of an intron may be adapted such that said RNA sequence of interest contains the correct reading frame for a protein to be expressed.

Said first or said second nucleotide sequence may contain further genes or coding sequences of interest, optionally with regulatory elements like a promoter, an IRES element etc. for endowing said cells with a further trait of interest. Two, three or more proteins or traits of interest may in this way be expressed. Further, complex nucleotide sequences may be co-integrated in a chromosome, whereby complex integration patterns may be obtained as exemplified in FIG. 12C. Cloning of vectors as those shown in FIG. 12A and B is a lot easier than cloning of a vector containing all the elements shown in FIG. 12C, which constitutes an important advantage of the process of the invention.

In a further embodiment (see FIG. 1 II), said plant cells or said plant is further provided with a third vector containing a third nucleotide sequence coding, in 5' to 3' direction, for
    a 3' part of an intron functional with said 5' part of an intron of said first nucleotide sequence,
    a middle part of said RNA sequence of interest, and
    a 5' part of an intron functional with said 3' part of an intron of said second nucleotide sequence.

In this case, expression of said trait of interest preferably requires formation of a transcription unit in a plant chromosome comprising sequences from all three vectors.

In a further embodiment, the method of the invention may be used for screening a set of first vectors and a set of second vectors for a combination of a first and a second vector, said combination giving rise to plants or plant cells endowed with a desired trait. This embodiment of the process of the invention comprises the following steps (A) and (B):
(A) providing plants or plant cells with a mixture of
    (i) a set of m first vectors each having a first nucleotide sequence with a first segment coding for a 5' part of said RNA sequence of interest, said 5' part of said RNA sequence of interest being selected from the set ($a_1$, $a_2$, . . . , $a_m$) and
    (ii) a set of n second vectors each having a second nucleotide sequence with a second segment coding for a 3' part of said RNA sequence of interest, said 3' part of said RNA sequence of interest being selected from the set ($b_1$, $b_2$, . . . , $b_n$),
    whereby
    m and n are independent of each other and both are integers of $>1$,
    said first vectors and said second vectors are adapted for producing different RNA sequences of interest,
(B) selecting transformed plants or plants cells endowed with a trait of interest.

Said set of first vectors and said set of second vectors may be libraries of first or second nucleotide sequences, respectively, in said vectors. For m=3 and n=2 as an example, plant cells expressing RNA sequences of interest $a_1b_1$, $a_1b_2$, $a_2b_1$, $a_2b_2$, $a_3b_1$, and $a_3b_2$ may be obtained that, by translation, may lead to different proteins of interest or traits of interest. Each plant cell or plant expressing a particular RNA sequence of interest represents a member of a library of plants obtained by the invention. Seeds of such plants may be produced for obtaining a library of plant seeds. In the form of seeds, the library may be easily stored and the library can be maintained or propagated if necessary. Step (B) of the above embodiments may then be carried out independent of step (A), e.g. a long time after carrying out step (A). This embodiment is particularly useful for shuffling and selecting for a combination of protein domains of a multi-domain protein.

In the above screening method, the largest combinatorial variety of traits of interest (and thus transgenic plants or plant cells) may be formed. A more special embodiment comprises the following steps (A) and (B):
(A) providing plants or plant cells with a mixture of
    (i) a first vector having a first nucleotide sequence with a first segment coding for a 5' part of said RNA sequence of interest a, and
    (ii) a set of n second vectors each having a second nucleotide sequence with a second segment coding for a 3' part of said RNA sequence of interest selected from the set ($b_1$, $b_2$, . . . , $b_n$),
    whereby
    n is an integer of $>1$,
    said first vector and said second vectors are adapted for expressing RNA sequences of interest of the type ($a_1b_1$, $a_1b_2$, . . . , $a_1b_n$) or the type ($b_1a_1$, $b_2a_1$, . . . , $b_na_1$),
(B) selecting transformed plants or plants cells endowed with a trait of interest.

Different RNA sequences of interest may then be formed, each containing a sequence portion from said first segment and a sequence portion from a second segment.

The first vector may e.g. provide translation regulatory sequences that render sequence portions from the second vectors translatable after assembly of a RNA sequence of interest containing a sequence portion of said first vector and a sequence portion of a vector of said set of second vectors.

The overall process of the invention is of sufficient efficiency for enabling routine applications of the process of the invention. For example, screening of DNA libraries for a useful trait can be performed in planta with a low danger of missing library members that are not compatible with the prokaryotic systems used for cloning in traditional approaches. This allows to combine the processes of vector engineering (e.g. for functional genomics or directed evolution purposes) with the creation of stable transformants, thus significantly speeding up the process of screening for desired combinations of genetic elements under test. It also has an additional advantageous feature, as it allows to include residential regulatory elements into the screening process by entrapping between the 5' and 3' intron sequences, e.g. during "intronization" process.

The process of the invention has combinatorial variability at the level of primary transformants, thus allowing to combine together in one experiment directed evolution of coding sequences of interest (e.g. domain shuffling of a multi-domain protein of interest) and generation and selection for primary transformants exhibiting the trait of interest.

The process of the invention has many important applications, among which its use in DNA library screening, gene function analysis and functional genomics, and directed evolution including gene shuffling may be mentioned. Moreover, complex and/or large DNA sequences of interest to be introduced in a plant chromosome can be assembled in planta from smaller precursors (see FIG. 12). The process of the invention can, however, also be used for introducing a gene to be expressed in a chromosome of a plant cell or plant. In an important embodiment, all genes and/or coding sequences and/or expressible sequences of said DNA sequence of interest integrated into a chromosome are of plant origin, whereby no unnatural sequences can be outcrossed from the transgenic plants of the invention to other organisms.

A further important application of the invention is in processes of achieving environmentally safe plants having two transgenic sequences at the same loci on homologous chromosomes. As described in WO03/102197 (PCT/EP03/02986; incorporated herein by reference), such a combination of two transgenic sequences can together cause a trait of interest, but said trait of interest has a low likelihood of being transferred to progeny, since said two transgenic sequences will segregate in progeny. FIGS. 12 and 13 exemplify the use of the present invention in a process of producing environmentally safe plants.

Preferred Embodiments

A process of endowing a plant or plant cells with a trait of interest by expressing an RNA sequence of interest, said process comprising:
transforming plant cells or a plant by Agrobacterium-mediated transformation with a first T-DNA and a second T-DNA and selecting cells endowed with said trait of interest, wherein
said first T-DNA contains a first nucleotide sequence with a transcriptional promoter and a first segment coding, in 5' to 3' direction, for
 a 5' part of said RNA sequence of interest and
 a 5' part of an intron; and
said second T-DNA contains a second nucleotide sequence with a second segment coding, in 5' to 3' direction, for
 a 3' part of an intron and
 a 3' part of said RNA sequence of interest.

In a preferred process of the invention, said trait of interest is caused by expressing a protein of interest. Such preferred process may be a process of endowing a plant or plant cells with a trait of interest by expressing a protein of interest, said process comprising: providing plant cells or a plant with a first vector and a second vector and selecting cells endowed with said trait of interest, wherein
said first vector contains a first nucleotide sequence with a first segment coding, in 5' to 3' direction, for
 an N-terminal part of said protein of interest and
 a 5' part of an intron; and
said second vector contains a second nucleotide sequence with a second segment coding, in 5' to 3' direction, for
 a 3' part of an intron and
 a C-terminal part of said protein of interest.

In preferred embodiments of the invention, said first and said second vector are incapable of recombining with each other by site-specific recombination. The incapability of recombining may be due to a lack of a site-specific recombination site on said first or on said second vector or it may be due to the absence of a site-specific recombinase that could recognize site-specific recombination sites on said vectors.

I—assembly by transcription and splicing of an RNA sequence of interest (AB) containing sequences encoded by a first (A) and a second (B) nucleotide sequence of a first and a second vector, respectively.
II—assembly by transcription and splicing of an RNA sequence of interest (ACB) from three different nucleotide sequences from three vectors (A, C and B). Third vector C contains a third nucleotide sequence with a third segment encoding in 5' to 3' direction:
 a 3' part of an intron preferably functional with said 5' part of an intron of said first nucleotide sequence,
 a middle part of said RNA sequence of interest, and
 a 5' part of an intron preferably functional with said 3' part of an intron of said second nucleotide sequence.
III—assembly by transcription and splicing of various RNA sequences of interest ($A_n B_n$) from a library of the vectors A and a library of vectors B, wherein n is the number of vectors in the library.

Figure 2:
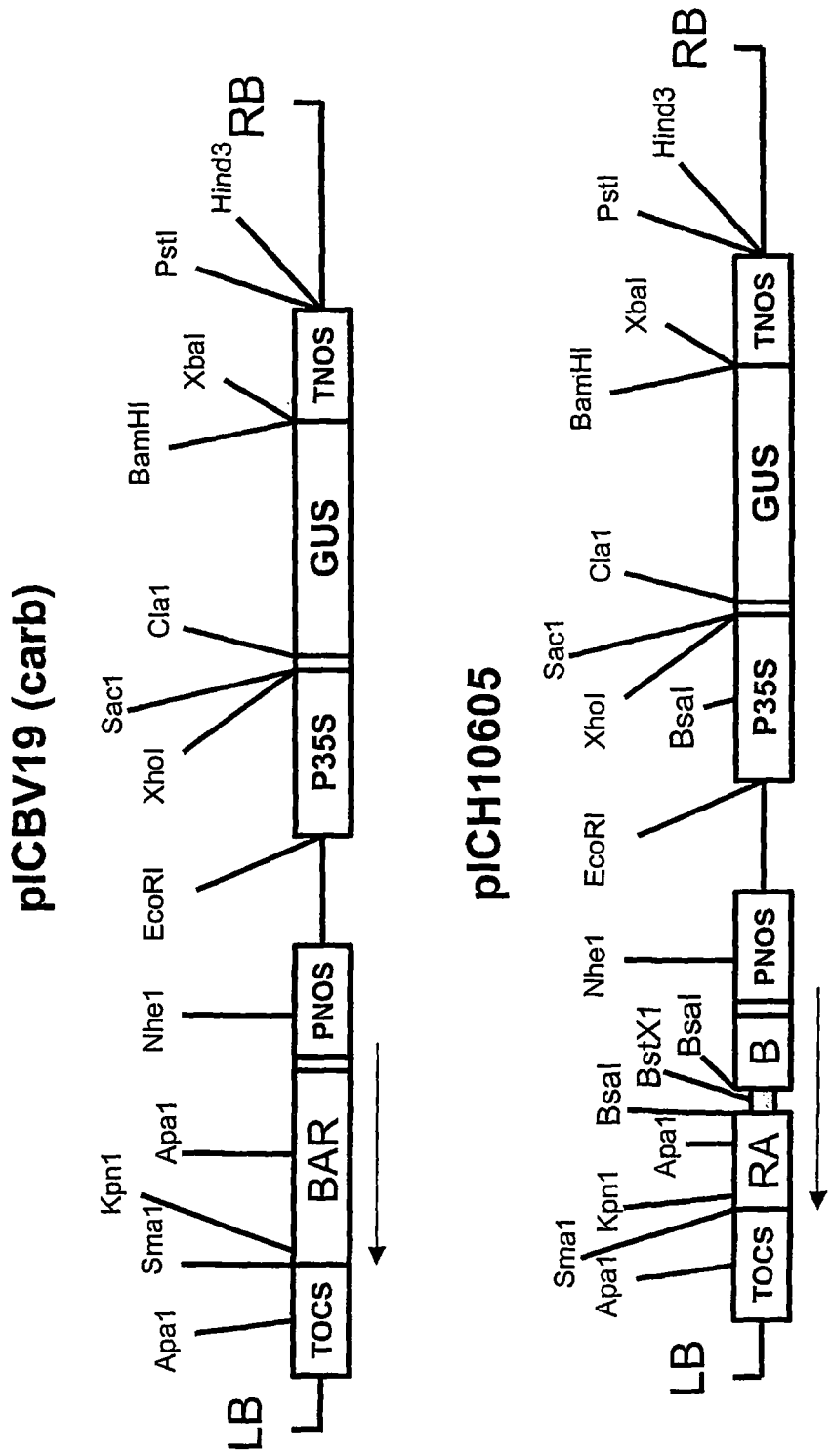

FIG. 2 depicts schematically the T-DNA regions of binary vectors plCBV19 and pICH10605. GUS—beta-glucuronidase gene; P35S—CaMV35S promoter; BAR—phosphinothricin acetyltransferase gene (pICH10605 has intron disrupting BAR coding sequences); PNOS—promoter of agrobacterial nopaline synthase gene; TNOS—transcription termination region of agrobacterial nopaline synthase gene; TOCS—transcription termination region of octopine synthase gene.

Figure 3:
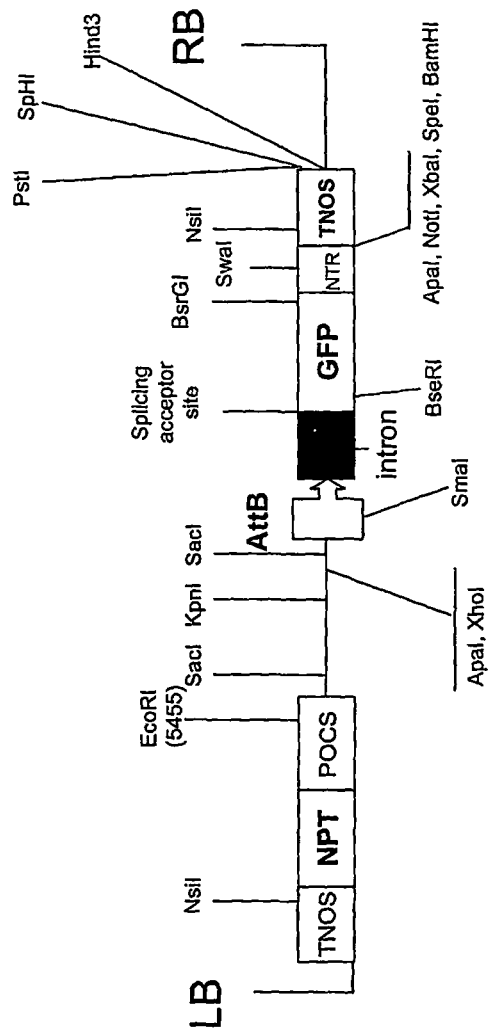

FIG. 3 depicts schematically the T-DNA region of binary vector pICH7410. GFP—gene encoding green fluorescent protein; NPT—neomycin phosphotransferase II gene conferring resistance to kanamycin; POCS—promoter region of agrobacterial octopine synthase gene; NTR—3' non-translated region of tobacco mosaic virus (TMV) RNA; AttB—recombination site.

Figure 4:
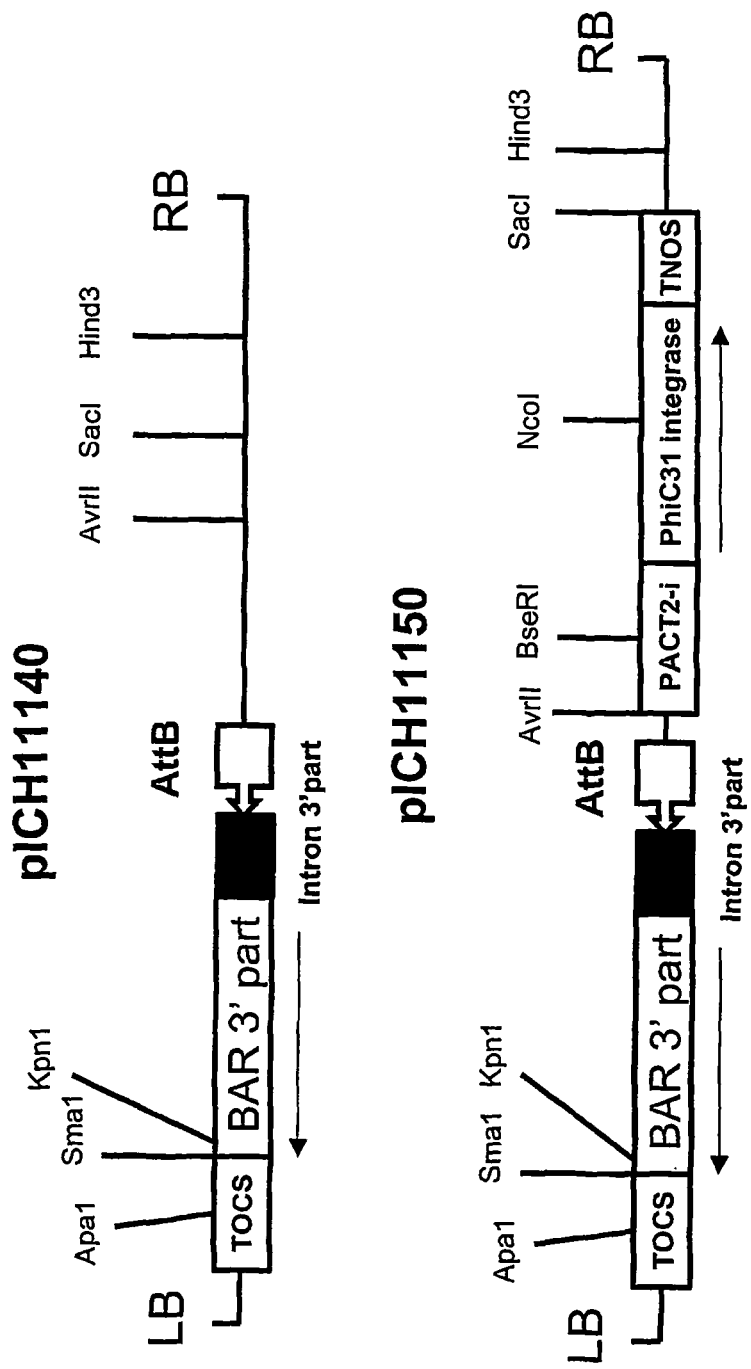

FIG. 4 depicts schematically the T-DNA regions of plasmids pICH11140 and pICH11150. PACT2-i-—promoter of the *Arabidopsis* actin2 gene with first intron.

Figure 5:
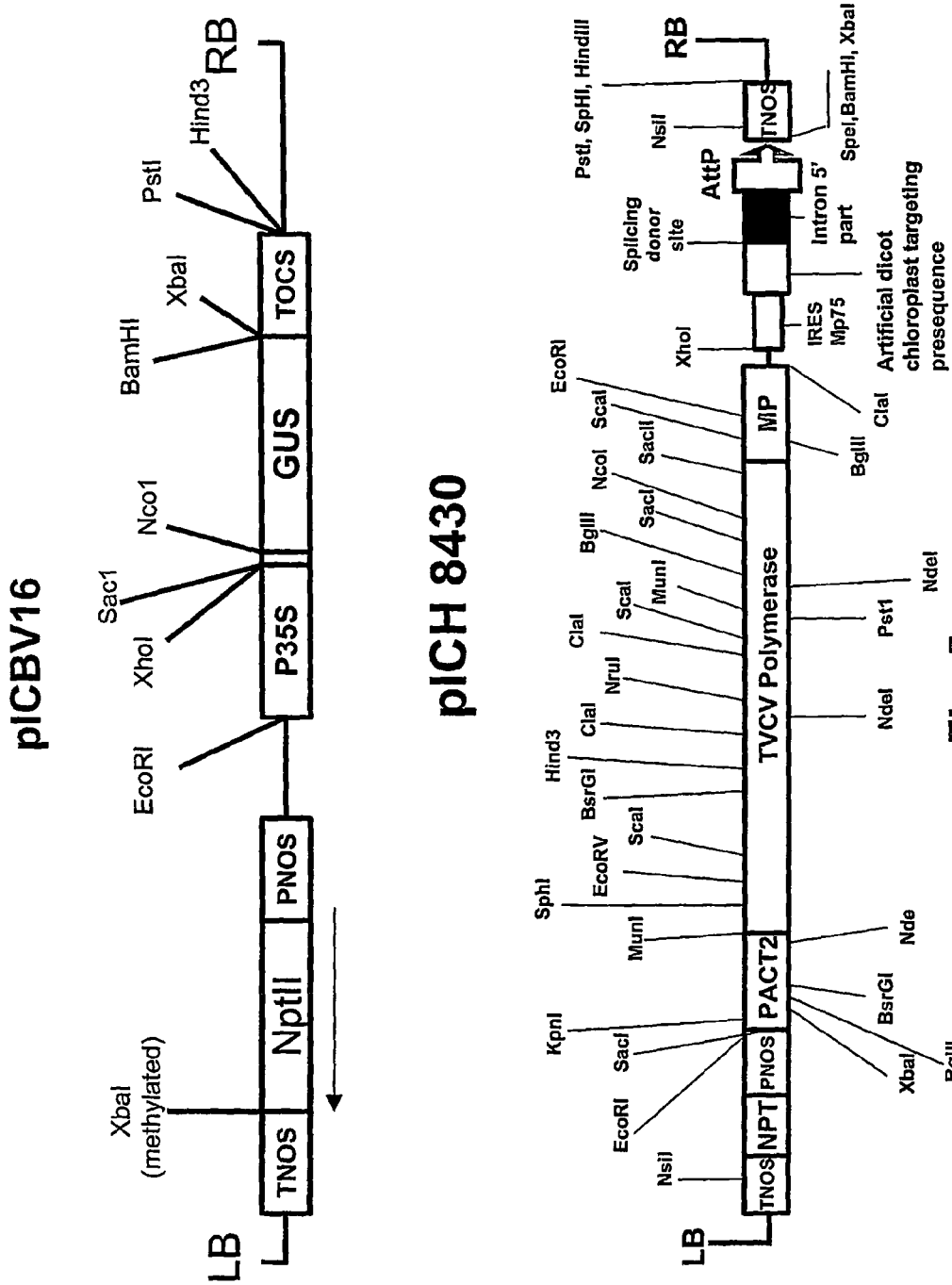

FIG. 5 depicts the T-DNA regions of the binary vectors plCBV16 and pICH8430. PACT2—promoter of the *Arabidopsis* actin2 gene; TVCV polymerase—RNA-dependent RNA polymerase of turnip vein-clearing virus (TVCV); MP—tobamoviral movement protein; IRESmp75—IRES of crTMV movement protein.

Figure 6:
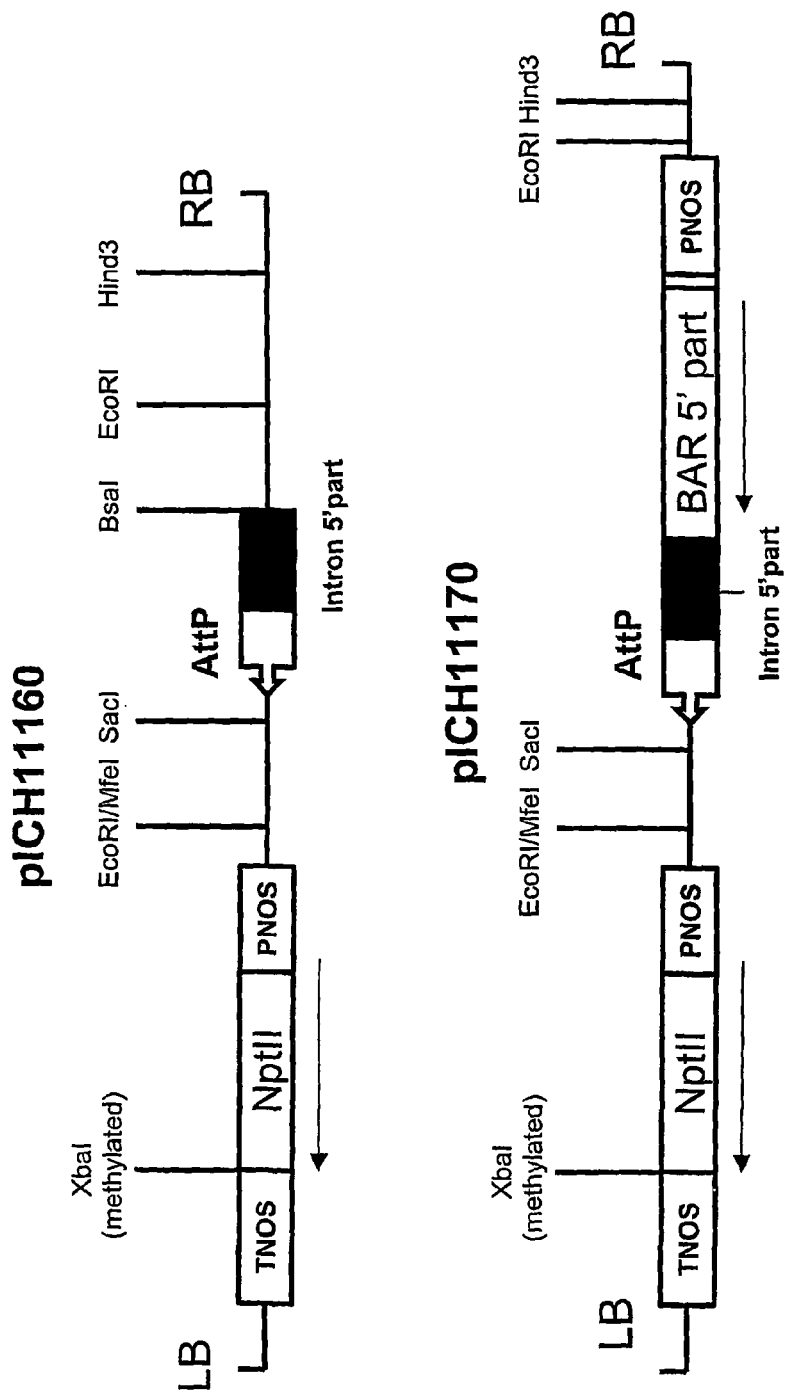

FIG. 6 depicts schematically the T-DNA regions of the binary vectors pICH11160 and pICH11170.

Figure 7:
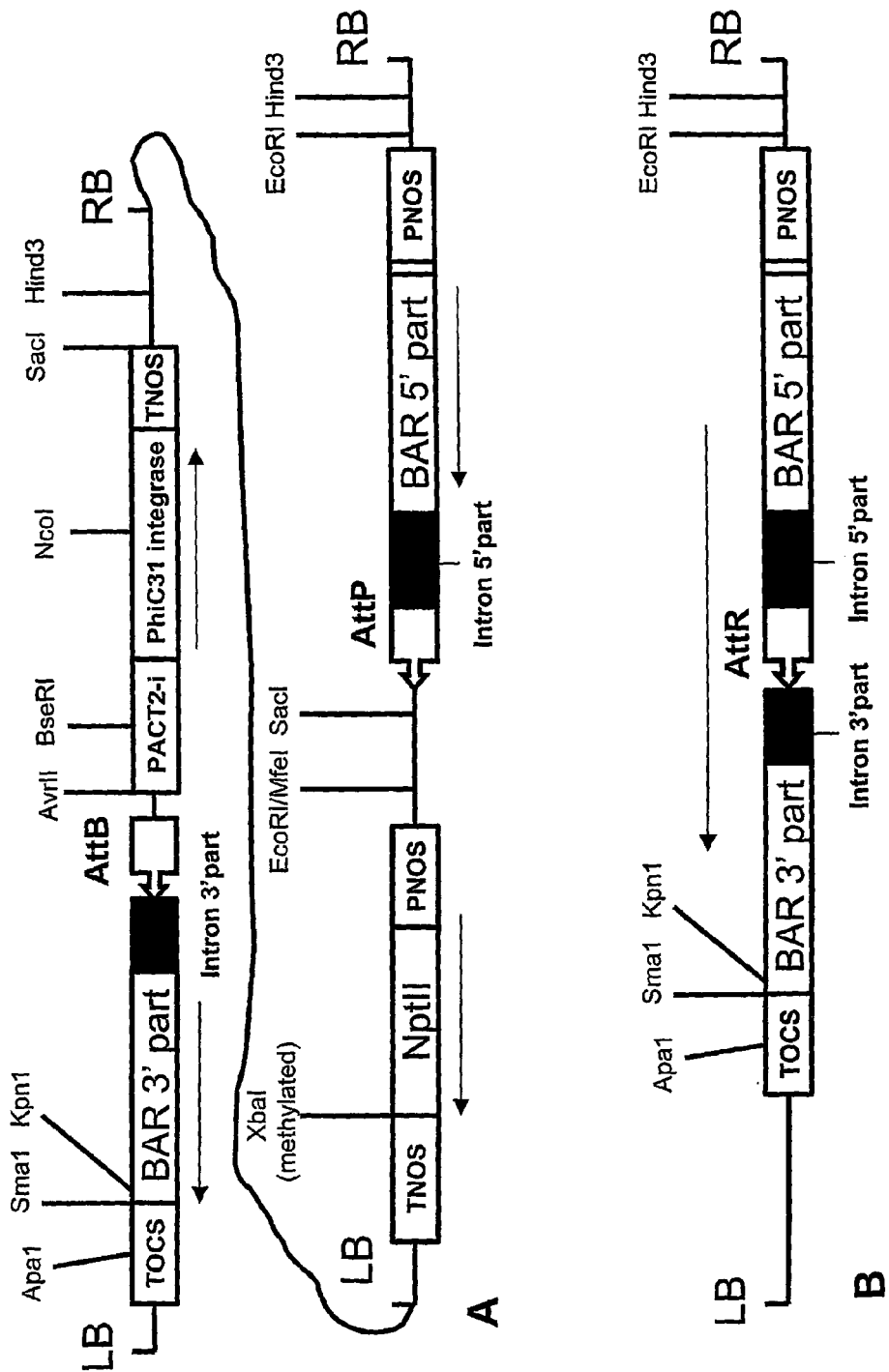

FIG. 7 depicts schematically the T-DNA regions resulting from (A) co-integration and (B) site-specific recombination between T-DNAs of pICH11150 and pICH11170. The T-DNA region carries a BAR gene interrupted by an intron containing an AttR site. Intron splicing after transcription allows expression of a functional BAR protein.

Figure 8:
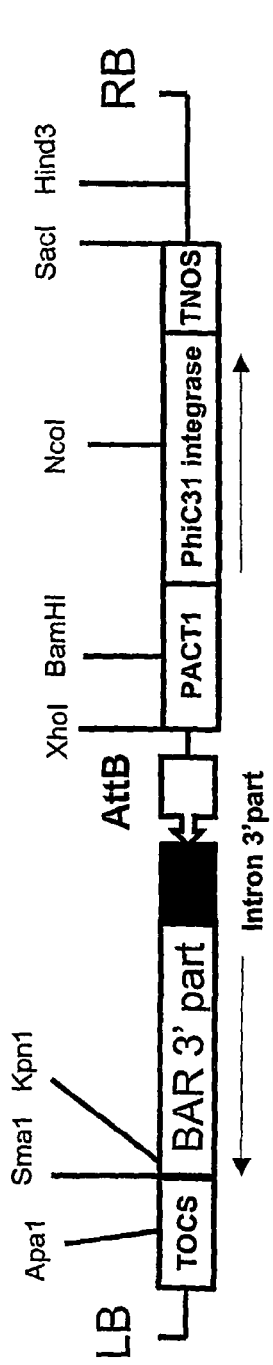
Figure 8:
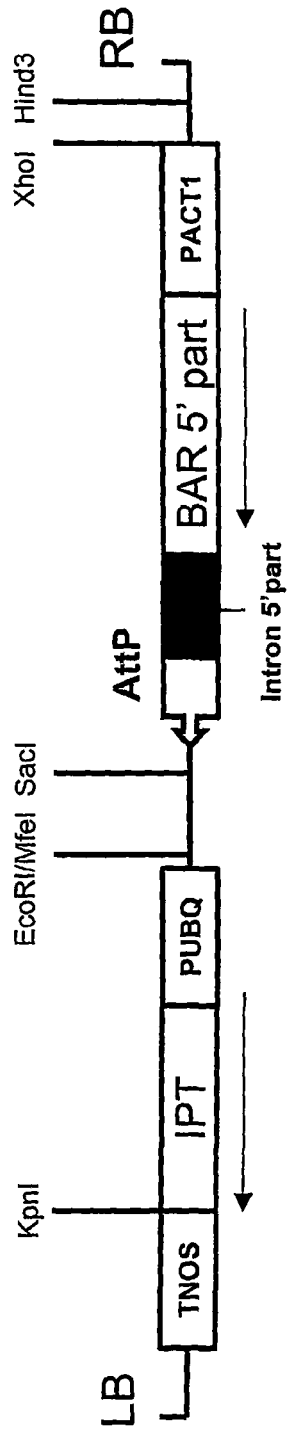

FIG. 8 depicts schematically the T-DNA regions of the binary vectors pICH12022 and pICH12031 designed for transformation of monocotyledonous plants. PUBQ—promoter of maize ubiquitin gene; PACT1—promoter of rice actin1 gene; IPT—gene encoding for isopentenyl transferase.

Figure 9:
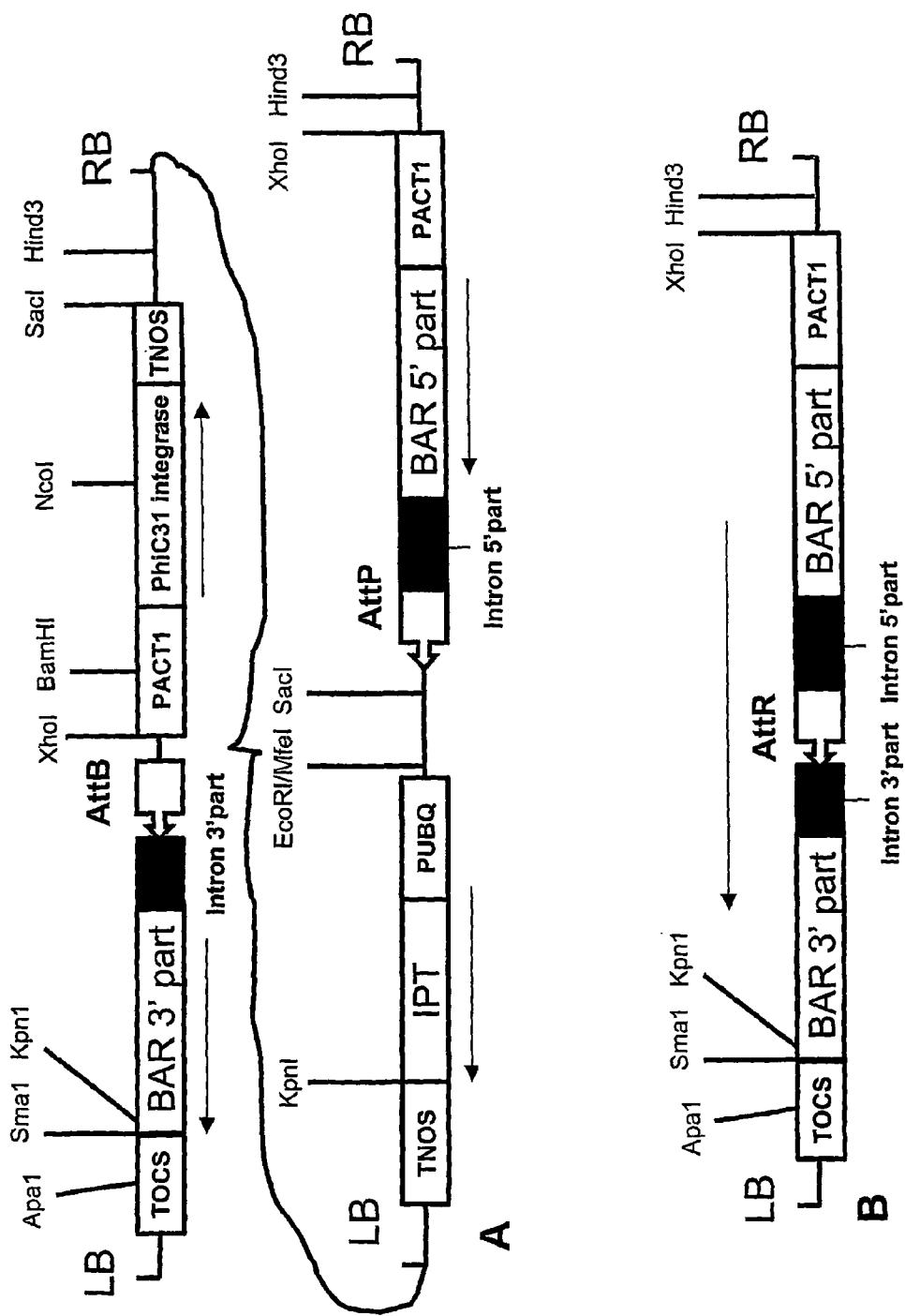

FIG. 9 depicts schematically the T-DNA regions resulting from (A) co-integration and (B) site-specific recombination between the T-DNA regions of binary vectors pICH12022 and pICH12031. The region carries a functional BAR gene interrupted by an intron under control of the rice actin1 promoter PACT1.

Figure 10:
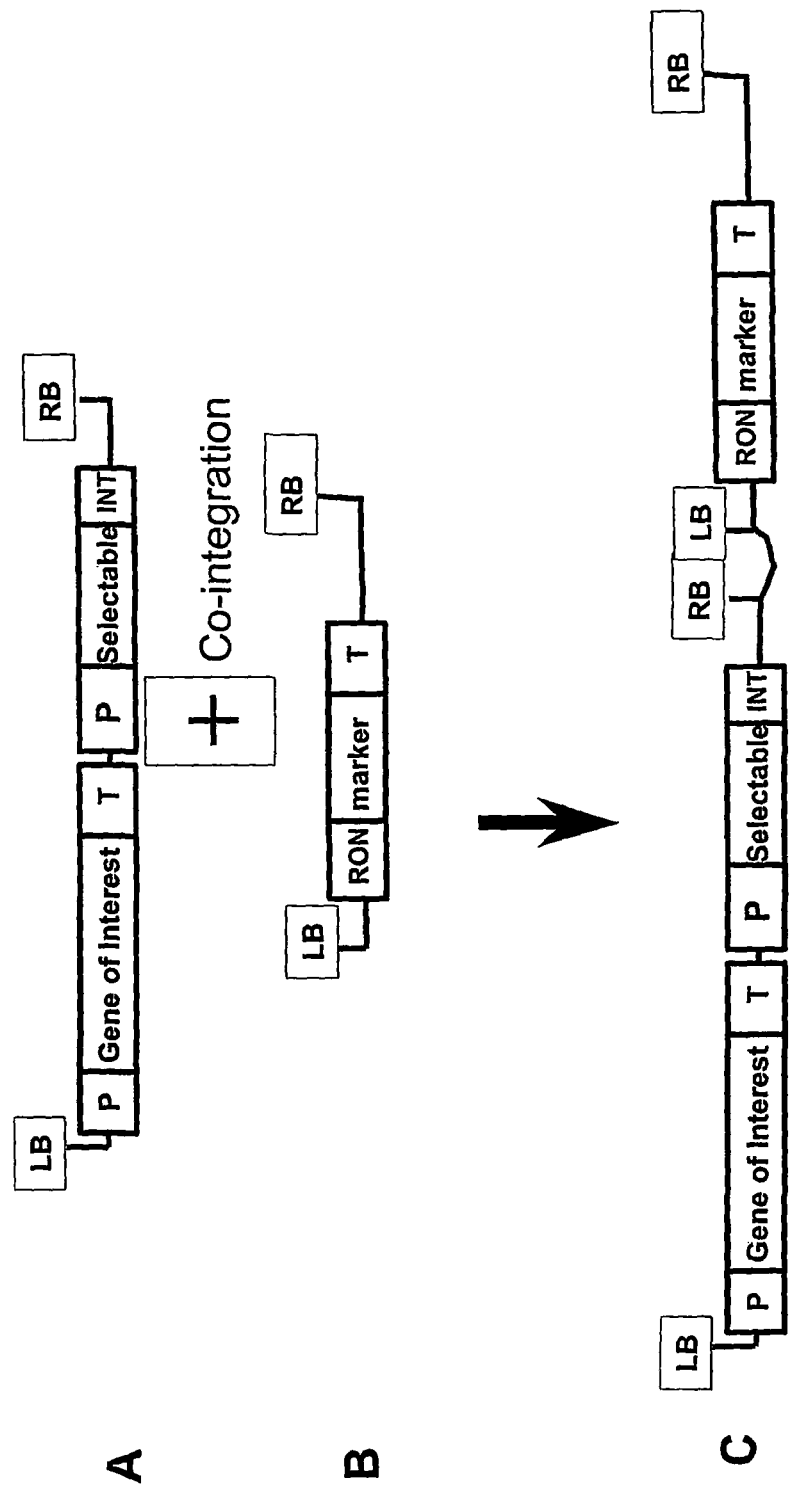

FIG. 10 depicts a scheme of co-integrating two T-DNAs (A and B) including assembly of a functional selectable marker gene from fragments of said selectable marker gene designated "Selectable" and "marker". Concomitantly, an intron (designated "INTRON") is assembled from intron fragments designated "INT" and "RON". P—promoter; T—transcription termination region; IRES—internal ribosome entry site. Selection for functional co-integration may be done by applying an antibiotic suitable for said selectable marker.

Figure 11:
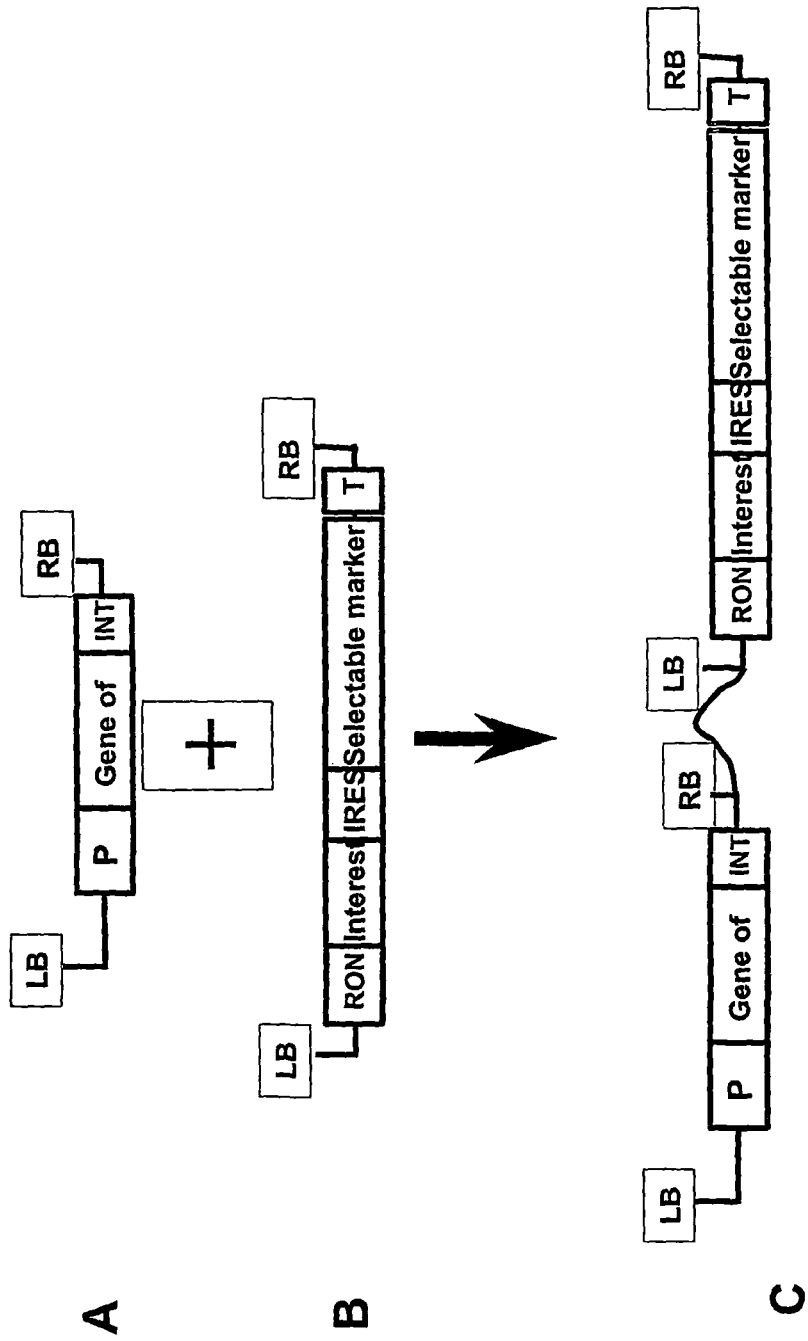

FIG. 11 depicts a scheme of co-integrating two T-DNAs (A and B) including assembly of a functional gene of interest from fragments of said gene of interest designated "Gene of" and "interest". Said co-integration also assembles a functional intron from a 5' part ("INT") and a 3' part ("RON") of said intron. The fragment of host chromosomal DNA (indicated by lines connecting boxes "INT" and "RON" and vector parts may be removed by RNA cis-splicing from a transcript formed under control of promoter "P". A selectable marker under translational control of an IRES element is rendered expressible by transcription under the control of the promoter. P—promoter; T—transcription termination region; IRES—internal ribosome entry site.

Figure 12:
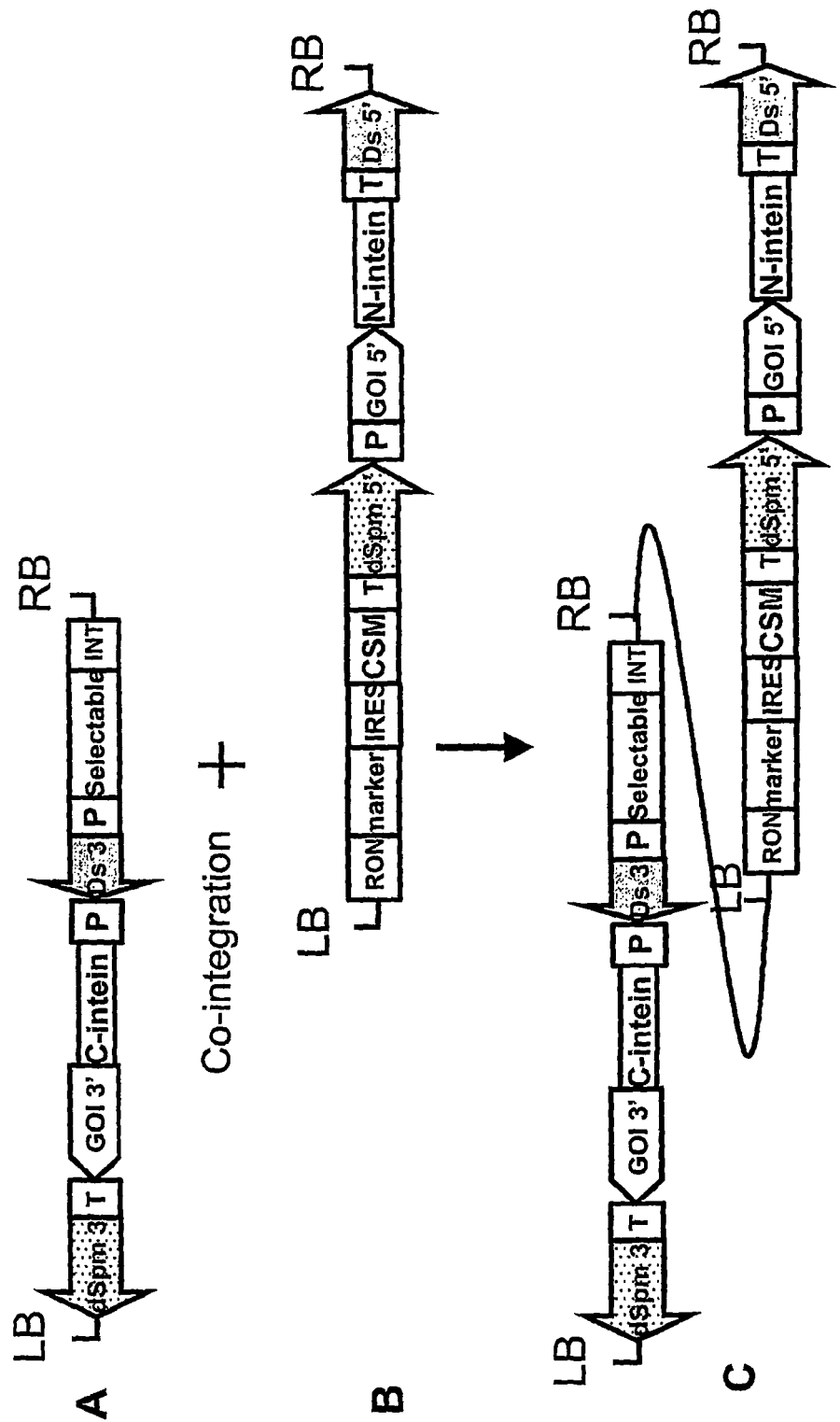

FIG. 12 depicts schematically co-integration in planta of vectors A and B to give co-integration pattern C. Plants or plant cells containing C may be used for obtaining environmentally safe transgenic plants (see FIG. 13) having transgenic sequences in allelic locations, i.e. a transgenic sequence in a locus on a chromosome and another transgenic sequence in the same locus on a homologous (allelic) chromosome. P—promoter; T—transcription termination region; CSM—counter-selectable marker; IRES—internal ribosome entry site; Ds (3' or 5')—non-autonomous transposable element (Ds) ends recognised by Ac transposase; dSpm (3' or 5')—non-autonomous transposable element (dSpm) ends recognised by Spm transposase; GOI—gene of interest.

Figure 13:
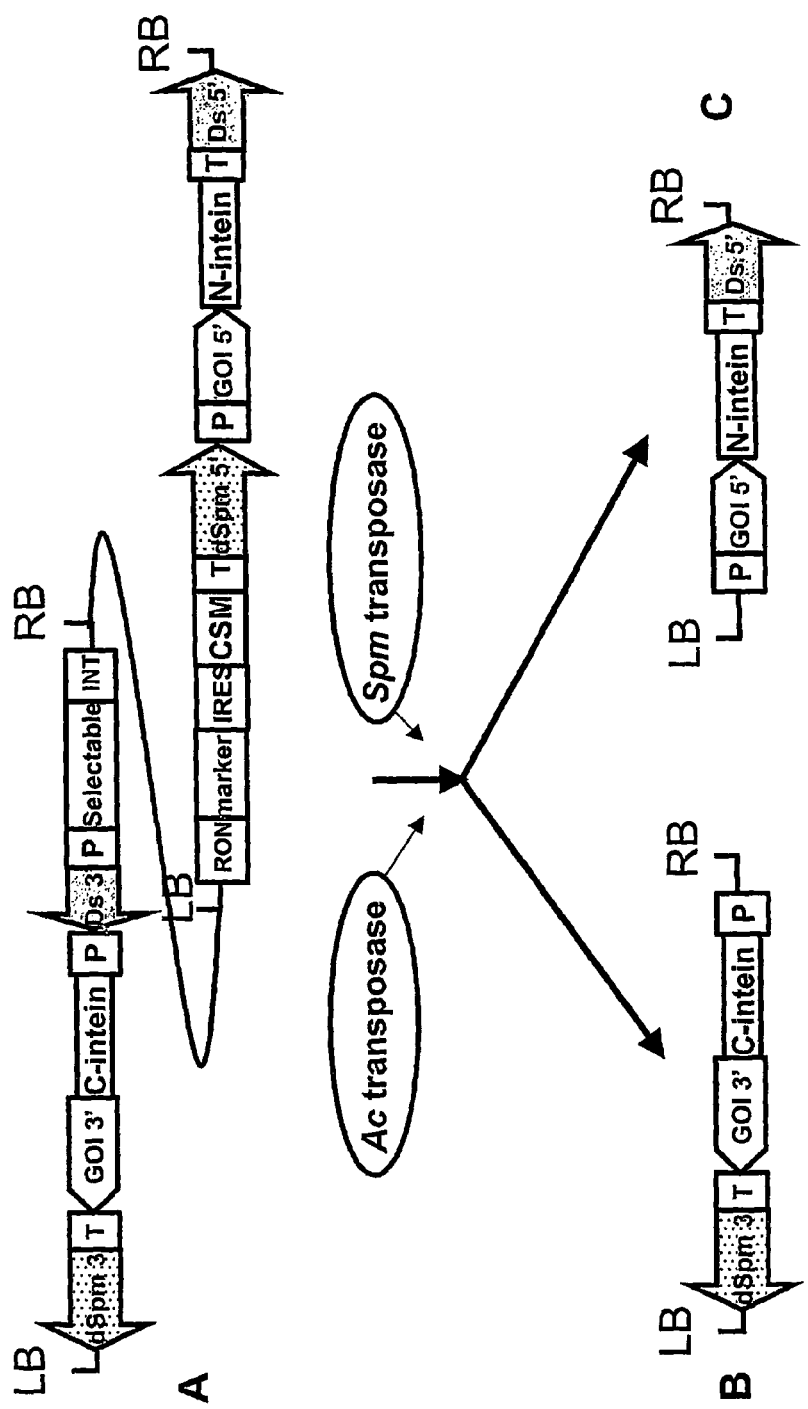

FIG. 13 depicts schematically a method of generating environmentally safe transgenic plants or plant cells with transgenic sequences in allelic locations. FIG. 13 (A) depicts a T-DNA integrated into a chromosome according to FIG. 12. Treatment of cells containing the T-DNA shown in (A) with Ac transposase allows to obtain cells containing the T-DNA shown in (B). Treatment of cells containing the T-DNA shown in (A) with Spm transposase allows to obtain cells containing the T-DNA shown in (C). Hybridizing cells or plants containing (B) with cells or plants containing (C) leads to cells or plants with T-DNAs (A) and (B) in allelic locations. P—promoter; T—transcription termination region; CSM—counter-selectable marker; IRES—internal ribosome entry site; Ds (3' or 5')—non-autonomous transposable element (Ds) ends recognised by Ac transposase; dSpm (3' or5')—non-autonomous transposable element (dSpm) ends recognised by Spm transposase; GOI—gene of interest.

Figure 14:
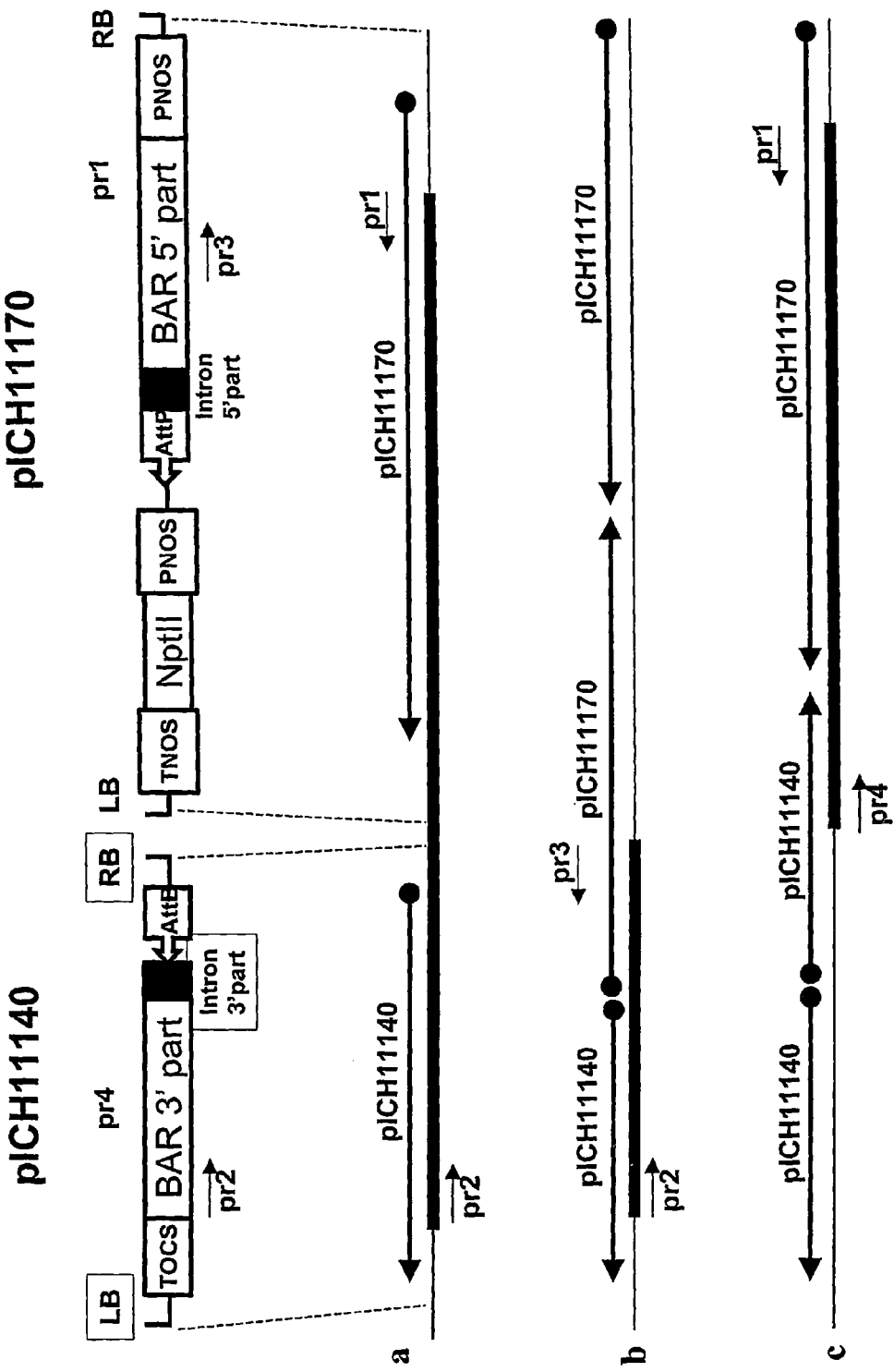

FIG. 14 depicts the T-bNA cointegration patterns that can provide for assembly of functional BAR transcript (see example 4). The positions of primers pr1-4, which were used for PCR analysis, are shown by arrows. The PCR amplified regions are shown by a solid line. Schematic representations and orientations of T-DNA regions in (a), (b) and (c) are indicated by arrows, where the oval arrow depicts the position of T-DNA right border (RB).

Figure 15:
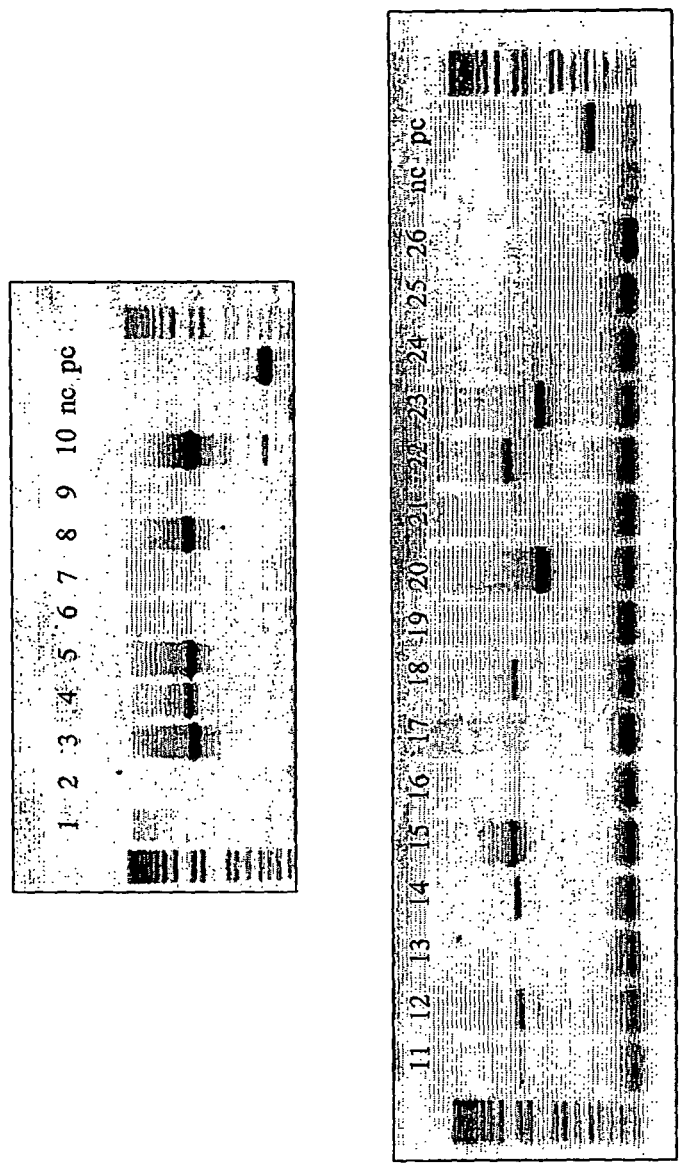

FIG. 15 shows the results of PCR analysis of PPT-resistant tobacco lines co-transformed with pICH11140 and pICH11170 constructs. Pr1 and Pr2 primers combination is used to test the T-DNA integration pattern shown in (a). Lanes 1-26—PCR analysis of PPT-resistant lines cotransformed pICH11140 and pICH11170; nc-negative control (wild type plant); pc-positive control, DNA from the plant transformed with plCBV19.

DETAILED DESCRIPTION OF THE INVENTION

In this invention we describe a process of rapid, inexpensive in planta assembly of a trait of interest from sequences derived from at least two vectors stably integrated into a plant chromosome. This approach allows inter alia for fast optimization of the sequences to be expressed by testing various transcription or translation units, units with different protein fusions or different protein targeting or post-translational modification, etc. It can be efficiently used for screening libraries of coding or regulatory sequences of interest. Another application of the invention is the design of environmentally safe transgenic plants which are unable to transfer the transgenic sequence of interest through an illicit gene transfer to other plants. Further, difficult cloning can be avoided during the design of complex DNA regions (e.g. showing instability during cloning procedures in bacterial cells) for stable nuclear transformation, as two or more complex DNA fragments can be functionally linked in planta after integration into a plant chromosome. Also, the invention offers the possibility of introducing two or more different T-DNAs into the same locus by selecting for co-integrated T-DNA regions resulting in intron-mediated assembly of an RNA sequence of interest encoding a selection marker. Thus, cointegration events may be selected. Subsequently, one of the two cointegrated T-DNA regions or parts thereof can be removed e.g. through transposition or site-specific recombination (cf. FIG. 13), providing for two different T-DNA regions in iso-allelic positions.

Said 5' and said 3' intron parts may be derived from a natural intron and derivatives thereof. There are different groups/classes of introns that are classified according to their internal organization and mechanism of splicing. Nuclear introns have in common the possession of GT-AG dinucleotides at the 5' and 3' ends and usually require spliceosome formation for their splicing. Group I and group II introns were named after introns found in different fungal mitochondrial genes. They are classified according to their internal organization but have in common the ability to autocatalyze their own splicing (self-splicing introns). There are different groups of introns and different RNA splicing reactions. Some introns require additional factors for functionality, whereas others do not (like self-splicing introns). There are introns that can perform cis-splicing and introns that perform trans-splicing reactions.

Nuclear introns are spliced via a snRNP-mediated (spliceosome-mediated) mechanism. There is abundant literature describing the mechanisms of cis-splicing including alternative splicing of nuclear genes in different eukaryotic organisms (for review see Adams et al., 1996, *Curr. Opin. Cell Biol.,* 8, 331-339; Hastings & Krainer, 2001, *Curr. Opin. Cell Biol.,* 13, 302-309). Naturally occurring trans-splicing with the involvement of a snRNP-mediated mechanism is described for an attachment SL (spliced leader) RNA to the 5' end of mRNAs in trypanosomes (Agabian, N., 1990, *Cell,* 61, 1157-1160; Luo et al., 1999, *J. Biol. Chem.,* 274, 31947-31954) and *Caenorhabditis elegans* (Hirsh & Huang, 1990, *Mol. Biol. Rep.,* 14, 115). These small "spliced leader" RNAs consist of a 5' exon fused to sequences that can functionally substitute for U1 snRNA in mammalian snRNP-splicing extracts. Similar trans-splicing of SL RNA was also shown in the chordates.

Group I and II introns have the ability to splice themselves out of pre-mRNA. This reaction can be performed in vitro by the RNA alone. Such RNAs with catalytic activities are generally called ribozymes. Both group I and group II introns are capable of splicing (including trans-splicing) in artificial systems (Been et al., 1986, *Cell*, 47, 207-216; Jacquier et al., 1986, *Science*, 234, 1099-1194; Jarrell et al., 1988, *Mol. Cell Biol.* 8, 2361-2366). Trans-splicing was also found for group II introns in split genes of chloroplasts (Kohchi et al., 1988, *Nucl. Acids Res.*, 16, 10025-10036), and for a group I intron in an artificial split gene in *Escherichia coli* (Galloway-Salvo et al., 1990, *J. Mol. Biol.*, 211, 537-549). Group I introns were first discovered in Tetrahymena thermophila rRNA (Cech, T. R., 1990, *Annu. Rev. Biochem.*, 59, 543-568). They require a U in the target sequence immediately 5' of the cleavage site and bind 4-6 nucleotides on the 5' side of the cleavage site. There are over 75 known members of this group up to now. They were found also in fungal and plant mitochondria (Richard & Dujon, 1997, *Curr. Genet*, 32, 175-181; Cho et al., 1998, *Proc. Natl. Acad. Sci. U.S.A*, 95, 14244-14249), chloroplasts (Turmel et al.1993, *J Mol. Biol.* 232, 446-46), phage T4 (Galloway et al., 1990, J. Mol. Biol., 211, 537-549), blue-green algae, and other organisms.

There are several developed approaches of using introns and engineered ribozymes which can be used to practice this invention (references cited above). They cover all known types of introns for engineering splicing events in eukaryotic cells. Ribozymes engineered on the basis of group I Tetrahymena introns (U.S. Pat. No. 6,015,794; Ayre et al., 1998, *Proc. Natl. Acad. Sci. U.S.A*, 96, 3507-3512), spliceosome-mediated (Puttaraju et al., 1999, *Nature Biotech.*, 17, 246-252; Liu et al., 2001, *Nature Biotech.*, 20, 47-52; U.S. Pat. No. 6,083,702) or group II intron-mediated trans-splicing (Mikheeva & Jarrell, 1996, *Proc. Natl. Acad. Sci. U.S.A*, 93, 7486-7490; U.S. Pat. No. 5,498,531) may be used for the present invention.

Since cis-splicing as used in the present invention is more efficient than trans-splicing, cis-splicing introns are preferred herein and introns for splicesome-mediated cis-splicing are most preferred. Such introns may be modified by inserting the additional heterologous sequences without loss of functionality, which is of particular importance for this invention, as host chromosomal sequences may be present between said 5' part of an intron and said 3' part of an intron after integration of said vectors.

Many nuclear introns can be used to practice this invention. Examples of such introns include the introns from rice tpiAct1, and salT genes (Rethmeier et al., 1997, *Plant J.*, 12, 895-899; Xu et al., 1994, *Plant Physiol.*, 100, 459-467; McElroy et al., 1990, *Plant Cell*, 2, 163-171); from the maize Adh1, GapA1, actin and Bz1 genes (Callis et al., 1987, *Genes Dev.*, 1, 1183-11200; Donath et al., 1995, *Plant Mol. Biol.*, 28, 667-676; Maas et al., 1991, *Plant Mol. Biol.*, 16, 199-207; Sinibaldi & Mettler, 1992, in W E Cohn, K Moldave, eds, *Progress in Nucleic Acids Research and Molecular Biology*, vol. 42, Academic Press, New York, pp. 229-257), from petunia rubisco gene SSU301 (Dean et al., 1989, *Plant Cell*, 1, 201-208), *Arabidopsis* A1 EF1α, UBQ10, UBQ3, PAT1 genes (Curie et al.,1993, *Mol. Gen. Genet.* 228, 428436; Norris et al., 1993, *Plant Mol. Biol.*, 21, 895-906; Rose & Last, 1997, *Plant J.*, 11, 455-464) and many others. There are no specific requirements regarding splitting a sequence encoding an intron for obtaining said 5' and said 3' part. However, it is preferred to split the intron at a site that is at similar distance from the 5' and the 3' ends of the intron in order not to disturb the splicing ability of the intron. Introns of different size (as small as 50 bp and as big as several Kbp) can be used in order to practice this invention. The smallest usable introns may be limited to splice donor and acceptor sites which usually flank the internal intron sequences. The origin of the intron, its structure and size may be selected individually depending on the nature of the trait or protein of interest. Transient expression experiments may be used for testing the efficiency of a chosen intron or the corresponding intron parts.

The use of an intron in the invention has the further advantage that introduction of introns into coding regions usually leads to an increase of the efficiency of transgene expression in eukaryotic organisms including plants (Rethmeier et al., 1997, *Plant J.*, 12, 895-899; Bourdon et al., 2001, EMBO Rep., 2, 394-398; Rose & Beliakoff, 2000, *Plant Physiol.*, 122, 535-542; for review see Le Hir et al., 2003, *Trends Biochem. Sci.*, 28, 215-220).

Current methods of transient or constitutive transgene expression in plants usually employ introducing into plant cells assembled vector(s) with the gene(s) of interest This invention is preferably not concerned with transient expression of a sequence of interest The differences between transient and constitutive transgene expression are best exemplified, e.g. within the frame-work of plant functional genomics, where the use of viral vectors can relatively fast provide some initial information about a possible function of a transgene in some cases (WO993651; Kumagai et al., 1995, *Proc. Natl. Acad. Sci. U.S.A*, 95, 1679-1683). In many other cases, no information or artefacts are obtained. Further, use of viral vectors does not allow further study of transgene function, e.g. during plant development, etc. In addition, Agrobacteria or viral vectors as such may cause severe changes in the plant cells, thus making it difficult to study, for example, the functions of genes involved in plant-pathogen interactions. Stably transformed transgenic plants with different expression patterns (e.g. Inter- or intracellular compartmentalisation, tissue, organ or cell-specific expression) are required for detailed study of a gene of interest. According to the present invention, the assembly, optimization and identification of an RNA sequence or a trait of interest can be performed with high efficiency in planta, thus be combined with plant transformation as a one step procedure.

Figure 1:
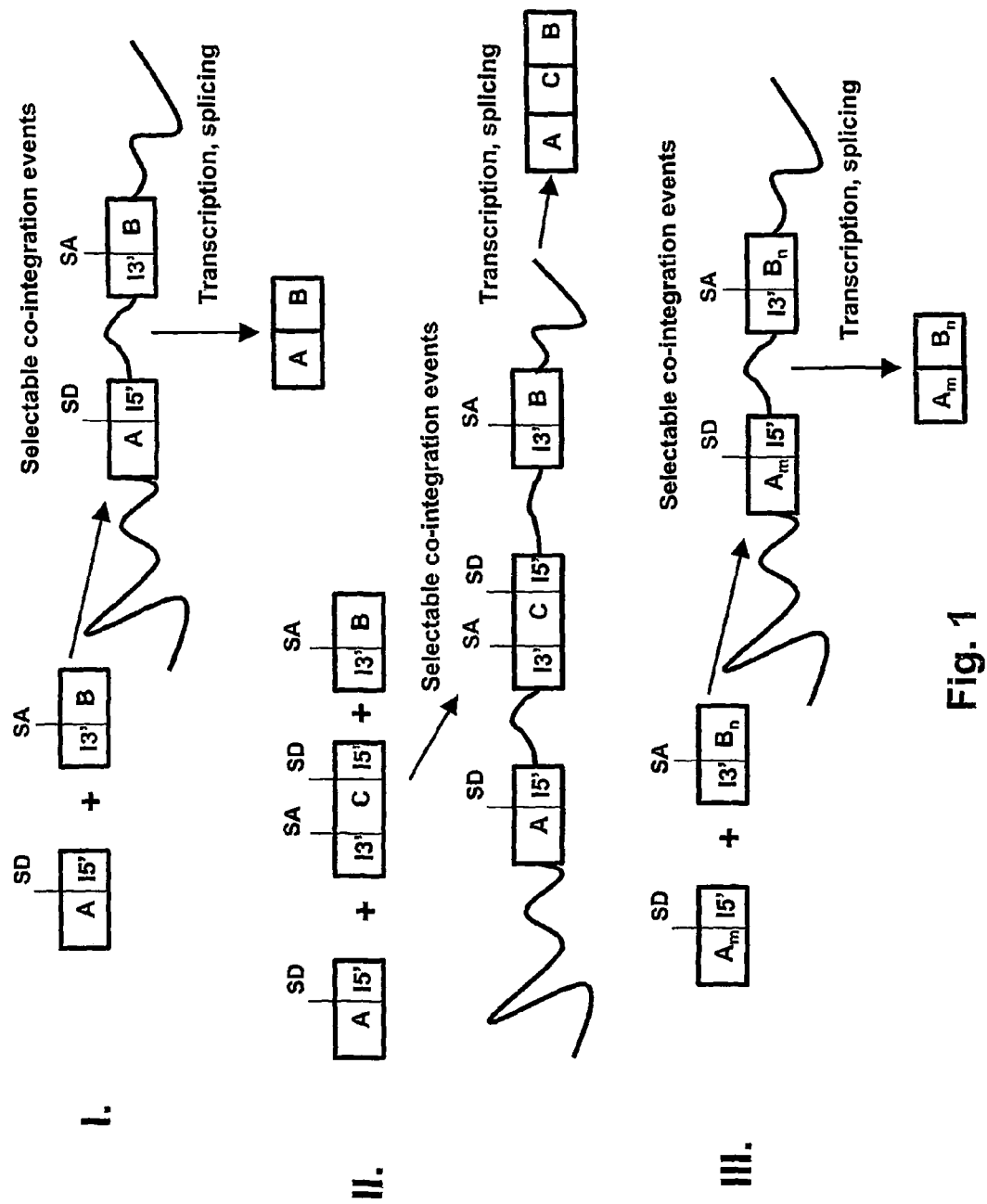
FIG. 1 shows schematically three general embodiments of the process of the invention. On the left, nucleotide sequences (A, B, C) of a first, a second, and optionally a third vector provided to plant cells are depicted (as boxes) that are stably integrated into a plant chromosome. integrated nucleotide sequences are depicted by boxes connected by a line that indicates the host chromosomal DNA. SD and SA stand for splice donor and splice acceptor sites, respectively. I5' and I3' designate 5' and 3' parts of an intron.

A general scheme of assembling a trait of interest from two or more vectors by co-integration is shown in FIG. 1. The simplest embodiment of the invention is the creation of an RNA sequence of interest AB from two co-integrated vectors A and B (FIG. 1, I). Such co-integration events should be selectable. This may be achieved e.g. if co-integration results in expression of a selection marker.

In one embodiment of the invention, a T-DNA region (FIG. 7) is assembled from two vectors represented by two other T-DNA regions (FIGS. 4 and 6, bottom) using integrase PhiC31-mediated recombination. The assembled T-DNA region may contain a functional BAR gene that is absent in said vectors, thus allowing selection for recombination events. The integrase necessary for assembly for the T-DNA region may be transiently provided by one of the vectors, pICH11150 (FIG. 4). Because of the irreversibility of the reactions catalyzed by PhiC31 integrase, said integrase can also be constitutively expressed by a genetically engineered plant or plant cell. By analyzing primary transformants transformed with said vectors, we surprisingly found that the majority of the transformants contained said T-DNA region depicted in FIG. 7-A instead of the recombination product depicted in FIG. 7-B. The selection of transformants having the integration pattern of FIG. 7A for Basta resistance was possible despite the large distance between the two parts of the sequences encoding BAR. This phenomenon is a result of efficient cis-splicing of the "intronised" region (region flanked by 5' and 3' intron parts)

including other transcriptional cassettes and host DNA sequences and paved the way for the development of this invention.

Another preferred embodiment of the invention comprises the generation of a co-integration product, notably for monocotyledonous plants (FIG. 9), from first and second vectors (FIG. 8). Said vectors are similar to those described above for dicot plant transformation, but contain monocot-specific transcriptional regulatory elements. Transformed plants provided for BAR expression, which can occur not only by site-specific recombination between said first and second vectors (FIG. 9-B), but also due to co-integration without recombination events taking place (FIG. 9-A).

Different methods may be used for providing a plant cell with said first and said second (or further) vectors. Said vectors may be transformed into plant cells by a Ti-plasmid vector carried by *Agrobacterium* (U.S. Pat. Nos. 5,591,616; 4,940,838; 5,464,763) or by particle or microprojectile bombardment (U.S. Pat. No. 05,100,792; EP 00444882B1; EP 00434616B1). Other plant transformation methods can also be used like microinjection (WO 09209696; WO 09400583A1; EP 175966B1), electroporation (EP00564595B1; EP00290395B1; WO 08706614A1) or PEG-mediated transformation of protoplasts etc. The choice of the method for vector delivery may depend on the plant species to be transformed. For example, microprojectile bombardment is generally preferred for monocot transformation, while for dicots, *Agrobacterium*-mediated transformation gives better results in general.

In the embodiment described above, we used *Agrobacterium*-mediated delivery of vectors into *Nicotiana* cells. However, said vectors may be introduced into plants in accordance with any of the standard techniques suitable for stable transformation of the plant species of interest. Transformation techniques for dicotyledons are well known in the art and include *Agrobacterium*-based techniques and techniques which do not require *Agrobacterium*. Non-*Agrobacterium* techniques involve the uptake of exogenous genetic material directly by protoplasts or cells. These techniques include PEG or electroporation mediated uptake, particle bombardment-mediated delivery and microinjection. Examples of these techniques are described in Paszkowski et al, EMBO J 3:2717-2722 (1984), Potrykus et al., Mol. Gen. Genet. 199:169-177 (1985), Reich et al., Biotechnology 4:1001-1004 (1986), and Klein et al., Nature 327:70-73 (1987). In each case, the transformed cells are regenerated to whole plants using standard techniques.

*Agrobacterium*-mediated transformation is a preferred technique for the transformation of dicotyledons because of its high transformation efficiency and its broad utility with many different species. The many crop species which may be routinely transformed by *Agrobacterium* include tobacco, tomato, sunflower, cotton, oilseed rape, potato, soybean, alfalfa and poplar (EP 0 317 511 (cotton), EP 0 249 432 (tomato), WO 87/07299 (*Brassica*), U.S. Pat. No. 4,795,855 (poplar)). *Agrobacterium* transformation typically involves the transfer of the binary vector carrying the foreign DNA of interest to an appropriate *Agrobacterium* strain, which may depend on the complement of vir genes carried by the host *Agrobacterium* strain either on a co-resident plasmid or chromosomally (Uknes et al., Plant Cell 5:159-169 (1993). The transfer of the recombinant binary vector to *Agrobacterium* may be accomplished by a triparental mating procedure using *E. coli* carrying the recombinant binary vector, a helper *E. coli* strain which carries a plasmid such as pRK2013, which is able to mobilize the recombinant binary vector to the target *Agrobacterium* strain. Alternatively, the recombinant binary vector may be transferred to *Agrobacterium* by DNA transformation (Höfgen & Willmitzer, Nucl. Acids Res. 16, 9877 (1988)).

Transformation of the target plant species by recombinant *Agrobacterium* usually involves co-cultivation of *Agrobacterium* with explants from the plant following protocols known in the art. Transformed tissue carrying an antibiotic or herbicide resistance marker present between the binary plasmid T-DNA borders may be regenerated on selectable medium. Preferred transformation techniques for monocots include direct gene transfer into protoplasts using PEG or electroporation techniques and particle bombardment into callus tissue.

The patent applications EP 0 292 435, EP 0 392 225 and WO 93/07278 describe techniques for the preparation of callus and protoplasts of maize, transformation of protoplasts using PEG or electroporation, and the regeneration of maize plants from transformed protoplasts. Gordon-Kamm, et al., Plant Cell 2:603-618 (1990), and Fromm, et al., Biotechnology 11:194-200 (1993), describe techniques for the transformation of elite inbred lines of maize by particle bombardment.

Transformation of rice can also be undertaken by direct gene transfer techniques utilizing protoplasts or particle bombardment. Protoplast-mediated transformation has been described for *Japonica*-types and *Indica*-types (Zhange, et al., Plant Cell Rep. 7:739-384 (1988); Shimamoto, et al., Nature 338:274-277 (1989); Datta, et al., Biotechnology 8:736-740 (1990)). Both types are also routinely transformable using particle bombardment (Christou, et al., Biotechnology 9:957-962 (1991)). *Agrobacterium*-mediated rice transformation is also applicable (Chan et al., 1993, *Plant Mol. Biol.,* 22, 491-506).

EP 0 332 581 describes techniques for the generation, transformation and regeneration of *Pooideae* protoplasts. Furthermore, wheat transformation is described by Vasil, et al., Biotechnology 10:667-674 (1992) using particle bombardment into cells of type C long-term regenerable callus, Vasil, et al., Biotechnology 11:1553-1558 (1993) and Weeks, et al,. Plant Physiol. 102:1077-1084 (1993) describe particle bombardment of immature embryos and immature embryo-derived callus.

Transformation of monocot cells such as *Zea mays* may be achieved by bringing the monocot cells into contact with a multiplicity of needle-like bodies on which these cells may be impaled, causing a rupture in the cell wall thereby allowing entry of transforming DNA into the cells (see U.S. Pat. No. 5,302,523). Transformation techniques applicable to both monocots and dicots are also disclosed in the following U.S. Pat. No. 5,240,855 (particle gun); U.S. Pat. No. 5,204,253 (cold gas shock accelerated microprojectiles); U.S. Pat. No. 5,179,022 (biolistic apparatus); U.S. Pat. Nos. 4,743,548 and 5,114,854 (microinjection); and U.S. Pat. Nos. 5,149,655 5,120,657 (accelerated particle mediated transformation); U.S. Pat. No. 5,066,587 (gas driven microprojectile accelerator); U.S. Pat. No. 5,015,580 (particle-mediated transformation of soy bean plants); U.S. Pat. No. 5,013,660 (laser beam-mediated transformation); U.S. Pat. Nos. 4,849,355 and 4,663,292.

Transgenic plant cells or plant tissue transformed by one of the methods described above by at least said first and said second vector may then be grown to full plants in accordance with standard techniques. Transgenic seeds can be obtained from transgenic flowering plants in accordance with standard techniques. Likewise, non-flowering plants such as potato and sugar beets can be propagated by a variety of known procedures. See, e.g., Newell et a. Plant Cell Rep. 10:30-34 (1991) (disclosing potato transformation by stem culture).

In one preferred embodiment, a mixture of a set of first vectors and/or a set of second vectors is used for assembling various RNA sequences of interest. Said RNA sequences of interest may be the result of random co-integration events between two sets of vectors (set $A_m$ and set $B_n$, FIG. 1, III) followed by transcription. A set of RNA sequences of interest of the type $a_m b_n$ may be generated in a set of plant cells by random co-integration of a set of first vectors ($A_1$, $A_2$, . . . , $A_m$) with a set of second vectors ($B_1$, $B_2$, . . . , $B_n$), wherein m and n are the number of different first vectors A and second vectors B, respectively. At least three different vectors are needed to endow the cell with at least two different RNA sequences of interest.

Examples of 5' and 3' parts of said RNA sequence of interest that are joint together may be coding sequences or parts thereof or any transcribed genetic elements. Herein, such a genetic element (or regulatory element) may be any sequence element that has a distinct genetic function preferably on RNA level. Examples of such genetic elements include: transcriptional enhancers, translational enhancers, recombination sites, transcriptional termination sequences, internal ribosome entry sites (IRESes), restriction sites, autonomously replicating sequences or origins of replications.

In this invention, the RNA sequence of interest may be derived from components from more than two vectors. In FIG. 1, II, the assembly of such an RNA sequence of interest containing sequence portions from three different vectors A, B and C is shown. However, the efficiency of assembly of such an RNA sequence of interest will be lower than in the case of two different vectors (FIG. 1, I).

The assembly of said RNA sequence of interest allows for the selection of plant cells having said first and said second vector suitably integrated according to the invention. One possible mechanisms of selection is the assembly of a functional selectable marker on RNA level as described in detail in examples 1-3 and shown in general in FIG. 10. The assembly of said RNA sequence of interest coding for a functional protein of interest may be an advantage, e.g. when the protein of interest (or a gene encoding it) is toxic for bacterial cells. The selectable marker in such cases can be a part of a bicistronic construct under control of an IRES element (FIG. 11). Co-integration of said vectors (A and B in FIG. 11) may lead to the formation of a transcription unit (C in FIG. 11) carrying the functional bicistronic construct with the gene of interest followed by an IRES-controlled selectable marker gene. The use of IRES elements in plants is known in the prior art (WO9854342; WO0246440; Dorokhov et al., 2002, *Proc. Natl. Acad. Sci. U.S.A,* 99, 5301-5306) and can be routinely practiced in combination with the present invention.

Assembly of complex vectors in planta from precursor vectors that are of simpler structure can be a further advantage, allowing to avoid complex cloning steps and/or manipulation with unstable DNA structures in bacterial cells. The assembly of the DNA sequence of interest for generating different derivative vectors in allelic position toward each other is shown in FIG. 12. Said DNA sequence of interest (FIG. 12,C) stably integrated into the plant chromosomal DNA can be further exposed to a transposase of choice (Ac or Spm, FIG. 13), allowing to remove the targeted sequences (flanked by Ds sequences for Ac or dSpm sequences for Spm). The final derivative vectors B and C (FIG. 13) are allelic in relation to each other and encode different parts of a gene of interest (GOI) that can be assembled through intein-mediated trans-splicing. This approach addresses biosafety issue, e.g. the control of transgene segregation, as the two fragments of the same gene providing for trait of interest would always segregate to different gametes due to their allelic location.

In the most preferred embodiment of this invention, no recombinase was used in the process of the invention for assembling said RNA sequence of interest. As it was mentioned above, the function of interest was expressed (PPT resistance) even when said two vectors, after integration into a chromosome, were separated by long stretches of host chromosomal and/or interfering T-DNA regions (Example 4; FIG. 14). We studied the organization of T-DNA integration sites of PPT resistant plants by using PCR (FIG. 15) and surprisingly found that the length of host chromosomal DNA separating said first and said second nucleotide sequence does not significantly interfere with the expression of said trait of interest, e.g. PPT resistance. The most likely explanation of this phenomenon is an efficient formation and processing of long transcripts containing two fragments of BAR gene coding sequences.

The transgenic plants or plant cells produced according to the invention may be used for many different purposes as mentioned above. In another application, plant cells having integrated said first and second vectors may in turn also be used as precursors for downstream processes. The integrated sequences (or vectors) may e.g. be induced to form an extrachromosomal DNA like an independently maintained episomal vector. This inducing may e.g. be achieved by crossing a transgenic plant obtained by the process of the invention with another plant that provides a factor capable of exerting the inducing function or triggering the formation of said extrachromosomal/episomal DNA. Alternatively, the formation of such an episomal DNA may be caused e.g. by transient expression of a factor (e.g. a transposase, a viral replicase, etc.) capable of triggering formation of the extrachromosomal/episomal DNA from said integrated sequences. Said episomal DNA may be capable of further reintegration (e.g. it may be or have properties of a transposable element) or be capable of independent maintenance during cell divisions (derivative of DNA viral vector).

The present invention is preferably carried out with higher, multi-cellular plants. Preferred plants for the use in this invention include any plant species with preference given to agronomically and horticulturally important species. Common crop plants for the use in present invention include alfalfa, barley, beans, canola, cowpeas, cotton, corn, clover, lotus, lentils, lupine, millet, oats, peas, peanuts, rice, rye, sweet clover, sunflower, sweetpea, soybean, sorghum triticale, yam beans, velvet beans, vetch, wheat, wisteria, and nut plants. The plant species preferred for practicing of this invention are including but not restricted to:

Representatives of Gramineae, Compositeae, Solanaceae and Rosaceae.

Additionally, preferred species for use the invention, as well as those specified above, plants from the genera: *Arabidopsis, Agrosts, Allium, Antirrhinum, Apium, Arachis, Asparagus, Atropa, Avena, Bambusa, Brassica, Bromus, Browaalia, Camellia, Cannabis, Capsicum, Cicer, Chenopodium, Chichorium, Citrus, Coffea, Coix, Cucumis, Curcubita, Cynodon, Dactylis, Datura, Daucus, Digitalis, Dioscorea, Elaeis, Eleusine, Festuca, Fragaria, Geranium, Glycine, Helianthus, Heterocallis, Hevea, Hordeum, Hyoscyamus, Ipomoea, Lactuca, Lens, Lilium, Linum, Lolium, Lotus, Lycopersicon, Majorana, Malus, Mangifera, Manihot, Medicago, Nemesia, Nicotiana, Onobrychis,*

*Oryza, Panicum, Pelargonium, Pennisetum, Petunia, Pisum, Phaseolus, Phleum, Poa, Prunus, Ranunculus, Raphanus, Ribes, Ricinus, Rubus, Saccharum, Salpiglossis, Secale, Senecio, Setaria, Sinapis, Solanum, Sorghum, Stenotaphrum, Theobroma, Trifolium, Trigonella, Triticum, Vicia, Vigna, Vitis, Zea,* and the *Olyreae,* the *Pharoideae* and many others.

Within the scope of this invention the plant species, which are not included into the food or feed chain are specifically preferred for pharmaceutical and technical proteins production. Among them, *Nicotiana* species are the most preferred, as the species easy to transform and cultivate with well developed expression vectors (especially viral vectors) systems.

Genes of interest, their fragments (functional or non-functional) and their artificial derivatives that can be expressed in plants or plants cells using the present invention include, but are not limited to: starch modifying enzymes (starch synthase, starch phosphorylation enzyme, debranching enzyme, starch branching enzyme, starch branching enzyme II, granule bound starch synthase), sucrose phosphate synthase, sucrose phosphorylase, polygalacturonase, polyfructan sucrase, ADP glucose pyrophosphorylase, cyclodextrin glycosyltransferase, fructosyl transferase, glycogen synthase, pectin esterase, aprotinin, avidin, bacterial levansucrase, *E. coli* gIgA protein, MAPK4 and orthologues, nitrogen assimilation/metabolism enzyme, glutamine synthase, plant osmotin, 2S albumin, thaumatin, site-specific recombinase/integrase (FLP, Cre, R recombinase, Int, SSVI integrase R, integrase phiC31, or an active fragment or variant thereof, oil modifying enzymes (like fatty acids desaturases, elongases etc), isopentenyl transferase, Sca M5 (soybean calmodulin), coleopteran type toxin or an insecticidally active fragment, ubiquitin conjugating enzyme (E2) fusion proteins, enzymes that metabolise lipids, amino acids, sugars, nucleic acids and polysaccharides, superoxide dismutase, inactive proenzyme form of a protease, plant protein toxins, traits altering fiber in fiber producing plants, Coleopteran active toxin from *Bacillus thuringiensis* (Bt2 toxin, insecticidal crystal protein (ICP), CrylC toxin, delta endotoxin, polyopeptide toxin, protoxin etc.), insect specific toxin AaIT, cellulose degrading enzymes, E1 cellulase from *Acidothermus celluloticus,* lignin modifying enzymes, cinnamoyl alcohol dehydrogenase, trehalose-6-phosphate synthase, enzymes of cytokinin metabolic pathway, HMG-CoA reductase, *E. coli* inorganic pyrophosphatase, seed storage protein, *Erwinia herbicola* lycopen synthase, ACC oxidase, pTOM36 encoded protein, phytase, ketohydrolase, acetoacetyl CoA reductase, PHB (polyhydroxybutanoate) synthase, enzymes involved in the synthesis of polyhydroxylalkanoates (PHA), acyl carrier protein, napin, EA9, non-higher plant phytoene synthase, pTOM5 encoded protein, ETR (ethylene receptor), plastidic pyruvate phosphate dikinase, nematode-inducible transmembrane pore protein, trait enhancing photosynthetic or plastid function of the plant cell, stilbene synthase, an enzyme capable of hydroxylating phenols, catechol dioxygenase, catechol 2,3-dioxygenase, chloromuconate cycloisomerase, anthranilate synthase, *Brassica* AGL15 protein, fructose 1,6-biphosphatase (FBPase), AMV RNA3, PVY replicase, PLRV replicase, potyvirus coat protein, CMV coat protein, TMV coat protein, luteovirus replicase, MDMV messenger RNA, mutant geminiviral replicase, *Umbellularia californica* C12:0 preferring acyl-ACP thioesterase, plant C10 or C12:0 preferring acyl-ACP thioesterase, C14:0 preferring acyl-ACP thioesterase (luxD), plant synthase factor A, plant synthase factor B, D6-desaturase, protein having an enzymatic activity in the peroxysomal b-oxidation of fatty acids in plant cells, acyl-CoA oxidase, 3-ketoacyl-CoA thiolase, lipase, maize acetyl-CoA-carboxylase, 5-enolpyruvylshikimate -3-phosphate synthase (EPSP), phosphinothricin acetyl transferase (BAR, PAT), CP4 protein, ACC deaminase, protein having posttranslational cleavage site, DHPS gene conferring sulfonamide resistance, bacterial nitrilase, 2,4D monooxygenase, acetolactate synthase or acetohydroxyacid synthase (ALS, AHAS), polygalacturonase, Taq polymerase, bacterial nitrilase, many other enzymes of bacterial or phage including restriction endonucleases, methylases, DNA and RNA ligases, DNA and RNA polymerases, reverse transcryptases, nucleases (Dnases and RNAses), phosphatases, transferases etc.

The present invention also can be used for the purpose of molecular farming and purification of commercially valuable and pharmaceutically important proteins including industrial enzymes (cellulases, lipases, proteases, phytases etc.) and fibrous proteins (collagen, spider silk protein, etc.). Human or animal health protein may be expressed and purified using described in our invention approach. Examples of such proteins of interest include inter alia immune response proteins (monoclonal antibodies, single chain antibodies, T cell receptors etc.), antigens including those derived from pathogenic microorganisms, colony stimulating factors, relaxins, polypeptide hormones including somatotropin (HGH) and proinsulin, cytokines and their receptors, interferons, growth factors and coagulation factors, enzymatically active lysosomal enzyme, fibrinolytic polypeptides, blood clotting factors, trypsinogen, a1-antitrypsin (AAT), human serum albumin, glucocerebrosidases, native cholera toxin B as well as function-conservative proteins like fusions, mutant versions and synthetic derivatives of the above proteins.

The above proteins and others can optimised for a desired purpose by introducing random mutations into their coding sequence or by gene shuffling methods. Screening for a protein having optimised properties for the desired purpose may then be done using the process of the present invention.

EXAMPLES

The following examples are presented to illustrate the present invention. Modifications and variations may be made without departing from the spirit and scope of the invention. The skilled person will be able to modify the examples below such that no site-specific recombination between said vectors can take place, e.g. by rendering the integrase gene unexpressible or unfunctional, or by eliminating the site-specific recombination sites.

Example 1

Vector Design for the Stable Transformation of Dicotyledonous Plants with a Split BAR Gene
Design of pICH11150

This construct was made on the basis of binary vector pICBV-19 (FIG. 2). As a first step of cloning, the target BsaI restriction sites for the intron insertion were introduced into the BAR gene (construct pICH10605, FIG. 2). The BasI enzyme cuts DNA outside of the recognition site, making 4 nucleotides overhang. In the case of pICH10605, the BasI enzyme was used to introduce splicing acceptor and donor sites for the consequent intron insertion. As a next step, PCR fragment amplified on pICH7410 (FIG. 3) construct with oligos int-ad-9 (SEQ ID No: 1)(5'-tttttggtc cgacctgcaa caataagaac aaaaagtcat aaatt-3') and attbpr11 (SEQ ID No: 2)

(5'-tttaagcttg agctctttcc taggctcgaa gccgcggtgc gggtg-3') was inserted into pICH10605 using BasI and HindIII restriction sites. The PCR fragment containing AttB and 3' part of intron as well as AvrII and SacI restriction sites replaced the GUS expression cassette and 5' part of BAR expression cassette. The T-DNA part of the resulting construct (pICH11140, FIG. 4) contained the 3' part of BAR expression cassette: AttB, 3' part of the intron, 3' part of BAR-gene and OCS terminator as well as AvrII and SacI restriction sites. As a final step of 3' construct cloning, a PhiC31 integrase expression cassette containing Arabidopsis actin 2 promoter, PhiC31 integrase and NOS terminator was introduced into pICH11140 using AvrII and SacI restriction sites. The final construct pICH11150 containing a 3' part of the BAR gene with AttB, a recombination site together with the 3' end of the intron, as well as PhiC31 integrase expression cassette is shown in FIG. 4.

Design of pICH11170

This construct was made on the basis of binary vector pICBV-16 (FIG. 5). The PCR fragment amplified from pICH8430 (FIG. 5) with oligos int-ad-10 (SEQ ID No: 3)(5'-tttaagcttg aattctttg gtctcaggta agtttcattt tcataattac aca-3') and attppr14 (SEQ ID No: 4)(5'-tttttcaatt ggagctcca cgcccccaac tgagagaac-3') was cut with HindIII and MfeI restriction enzymes and introduced into pICBV-16 digested with HindIII and EcoRI. The PCR fragment containing the 5' part of an intron and AttP as well as BasI and EcoRI restriction sites replaced the GUS expression cassette in intermediate construct pICH11160 (FIG. 6). As the final step of the cloning, EcoRI/BasI fragment of pICH10605 (FIG. 2) containing a NOS promoter and 5' part of BAR gene was inserted into pICH11160. The T-DNA region of the final construct pICH11170 is shown in FIG. 6.

Example 2

Agrobacterium-mediated Transformation of Nicotiana Tabacum (cv Petit Havana) with in Planta Assembled T-DNA Region The constructs pICH11150 and pICH11170 were immobilized into A. tumefaciens (GV3101) and used for Agrobacterium-mediated leaf discs transformation of Nicotiana plants (Horsh et al., 1985, Science, 227, 1229-1231) using 10 mg/L of phosphinothricin (PPT) as selectable marker. Regenerated tobacco plants were PCR analysed for the presence of an in planta assembled T-DNA region stably integrated into chromosomal DNA (FIG. 7) and for the absence of T-DNA regions of pICH11150 and pICH11170.

Example 3

Vector Design and Agrobacterium-mediated Transformation of Monocotyledonous Plants with Split BAR Gene For the design of constructs using a split BAR gene to monitor assembly of a desired T-DNA region in planta, the original constructs pICH11150 and pICH11170 (see example 1) were used. The construct pICH11150 was modified by replacing the Arabidopsis actin2 (PACT2-i,) promoter with rice actin1 (PACT1) promoter (McElroy D, et al., 1991, Mol Gen Genet., 231, 150-160) yielding construct pICH12022 (FIG. 8). The construct pICH11170 was modified by replacing the nopaline synthase promoter (PNOS) driving expression of the BAR gene fragment with the rice actin1 promoter (PACT1) and the NPTII expression cassette with IPT (isopentenyl transferase, Gene Bank Acc. No.: X14410) expression cassette under control of the maize ubiquitin gene promoter (PUBQ) (Christensen A H & Quail P H., 1996, Transgenic Res., 5, 213-218) yielding construct pICH12031 (FIG. 8). All manipulations for construct design were performed using standard cloning procedures (Sambrook, Fritsch & Maniatis, 1989, Molecular cloning: A laboratory manual, 2nd ed. Cold Spring Harbor, N.Y.: CSH Laboratory Press).

The line PEN3 of Pennisetum glaucum was used for Agrobacterium-mediated transformation with plasmids pICH12022 and pICH12031. Aliquotes of Agrobacterium tumefaciens AGL1 strain carrying either pICH12022 or pICH12031 were mixed together in equal proportions and used for transformation as described below.

The culture medium included Murashige and Skoog (MS) salts and vitamins: (Reference: Murashige, T. & Skoog, F. A 1962, Physiol. Plant., 15, 473-497,) with 2.0 mg/L of 2,4-D, which is 2,4-Dichorophenoxyacetic acid, 30 g/l sucrose and 0.3% gelrite. Regeneration medium contained a half-strength MS salts and vitamins with 20 g/L maltose, 1 mg/L IAA, 1 mg/L Zeatin and 0.6% gelrite.

Infection medium (IM) contained a half-strength MS salts and vitamins with 2 mg/L 2,4D, 10 g/L glucose, 60 g/L maltose, 50 mg/L ascorbic acid, 1 g/L MES (2-N-morpholinoethanesulfonic acid) and 40 mg/L Acetosyringone (AS). The pH of the medium was adjusted to 5.2 by 1 N KOH. Cocultivation medium (CM) was same as the IM (excluding ascorbic acid) and was solidified by adding 0.6% gelrite. Infection medium was filter sterilized, whereas all other media were autoclaved. AS, dissolved in DMSO (400 mg/mL), was added after sterilization.

Agrobacterial cultures (strains AGL1, EHA105, A4 etc.) with the appropriate binary plasmids were grown for 3 days at room temperature on LB2N (LB medium with 2 g/L NaCl and 1.5% agar) plates supplemented with the appropriate antibiotics. Bacteria were scraped from the plates and resuspended in IM in 50-mL falcon tubes. The tubes were fixed horizontally to a shaker platform and shaken at low speed for 4 to 5 h at room temperature. Optical density of the suspension was measured and OD600 was adjusted to 1.0.

Callus pieces were incubated in the Agrobacterial suspension for 3 hours at room temperature and transferred to the gelrite-solidified CM with 60 g/L maltose.

After 3 days of cultivation on CM, the calli were washed five times by half-strength MS medium with 60 g/L sucrose and transferred to the gelrite-solidified CM with 60 g/L sucrose and 5 mg/L phosphinothricin (PPT) and, in some cases, 150 mg/L Timentin. Phosphinothricin-resistant calli developed under selection were plated to the regeneration medium with 5 mg/L PPT.

The regenerating $PPT^R$ plant tissues were initially visually tested for the absence of functional IPT gene causing adventitious formation of shoots in hormone-free media (Ooms et al, 1983, Theor. Appl. Genet., 66, 169-172; Smigocki, A C & Owens, L D., 1989, Plant-Physiol., 91, 808-811; Smigocki, A C & Owens, L D. 1988, Proc. Natl. Acad. Sci. U.S.A, 85, 5131-5135). Secondary screening for plants carrying in planta assembled T-DNA region (FIG. 9) and for the absence of T-DNA regions from pICH 12022 and pICH 12031 were carried out by using PCR analysis of $PPT^R$ plant tissue for the presence of integrase PhiC31 and IPT gene sequences.

Example 4

Agrobacterium-mediated Transformation of Nicotiana Tabacum (cv Petit Havana) for Cointegration-mediated Trait Assembly The constructs pICH11140 and pICH11170 (FIG. 14) were immobilized into A. tumefaciens (GV3101) and used for *Agrobacterium*-mediated leaf discs transformation of *Nicotiana tabacum* plants (Horsh et al., 1985, *Science*, 227, 1229-1231) using 10 mg/L of phosphinothricin (PPT) as selective agent. Regenerated tobacco plants were PCR analysed for the presence of distinct T-DNAs cointegrated into chromosomal DNA in head-to-tail orientation (FIG. 14). Three integration patterns that could provide the assembly of the functional BAR transcript were tested. The presence of pattern (A) where LB of 5'T-DNA (pICH11170) is flanked by RB of 3'T-DNA (pICH11140) without any or with a relatively small space between T-DNA borders was checked by PCR with Pr1 (SEQ ID No: 5) (138fwd-bar: 5'-ccg tac cga gcc gca gga ac-3') and Pr2 (SEQ ID No: 6) (581rev-bar(5'-cag atc tcg gtg acg ggc agg ac-3') oligos. This integration pattern was found in 60% of tested plants (29 out of 48). The presence of pattern (B) where 5' and 3' T-DNAs are separated by the insertion of 5' T-DNA in the inverted orientation have been tested with Pr2 SEQ ID No: 6) (581rev-bar: 5'-cag atc tcg gtg acg ggc agg ac-3') and Pr3 (SEQ ID No: 7) (barpr2: 5'-gac cgt gct tgt ctc gat gta g-3') oligos. This integration pattern was found in 8% of tested plants (4 out of 48). The presence of pattern (C), where 5' and 3' T-DNAs are separated by the insertion of 3' T-DNA in the inverted orientation have been tested with Pr1 (SEQ ID No: 5) (138fwd-bar: 5'-ccg tac cga gcc gca gga ac-3') and Pr4 (SEQ ID No: 8) (barpr4: 5'-ggt ttc tgg cag ctg gac ttc-3') oligos. This integration pattern was not found among tested plants. Altogether, any of these patterns was detected in 69% of tested PPT-resistant plants (33 out of 48).

The invention claimed is:

1. A process of endowing a plant or plant cells with a trait of interest by expressing an RNA sequence of interest, said process comprising: transforming plant cells or cells of said plant with a first vector and a second vector and selecting cells endowed with said trait of interest, wherein
said first vector contains a first nucleotide sequence with a first segment coding, in 5' to 3' direction, for
(i) a 5' part of said RNA sequence of interest and
(ii) a 5' part of an intron; and
said second vector contains a second nucleotide sequence with a second segment coding, in 5' to 3' direction, for
(i) a 3' part of an intron and
(ii) a 3' part of said RNA sequence of interest;
wherein said 5' part of the intron and said 3' part of the intron leads to the formation of said RNA sequence of interest by splicing of a primary transcript containing said 5' part of said RNA sequence of interest, said 5' part of the intron, said 3' part of the intron, and said 3' part of said RNA sequence of interest, thereby forming said RNA sequence of interest as a secondary transcript, wherein said primary transcript is transcribed from a functional transcription unit comprising said first nucleotide sequence and said second nucleotide sequence, and wherein said second vector is devoid of a transcriptional promoter for transcribing said 3' part of the intron and said 3' part of said RNA sequence of interest.

2. The process according to claim 1, wherein said first vector and said second vector are adapted for integration of said vectors or parts of said vectors in a chromosome of said plant cells.

3. The process according to claim 2, wherein said chromosome is a nuclear chromosome.

4. The process according to claim 1, wherein said first and/or second vector is derived from a Ti-plasmid.

5. The process according to claim 1, wherein said first and said second nucleotide sequence are provided to said plant cells as T-DNA.

6. The process according to claim 1, wherein said first and said second vector are provided to said plant cells by *Agrobacterium*-mediated transformation.

7. The process according to claim 1, wherein said first nucleotide sequence contains a transcriptional promoter upstream of said first segment.

8. The process according to claim 1, comprising translation of said RNA sequence of interest to produce a protein of interest.

9. The process according to claim 8, wherein said first segment encodes a 5' part of said protein of interest and said second segment encodes a 3' part of said protein of interest.

10. The process according to claim 1, wherein said first segment or said second segment codes for a translation regulatory element.

11. The process according to claim 1, wherein said trait of interest is resistance against a selective agent for allowing selection of plant cells or plants having said first and said second vector cointegrated in a chromosome.

12. The process according to claim 1, wherein said first and/or said second nucleotide sequence contains a gene to be expressed for endowing said plant or said plant cells with a further trait of interest.

13. The process according to claim 1, wherein said first or said second vector cannot recombine with each other by site-specific recombination.

14. A process of endowing a plant or plant cells with a trait of interest by expressing an RNA sequence of interest, said process comprising: transforming plant cells or cells of said plant with a first vector and a second vector and selecting cells endowed with said trait of interest, wherein said first vector contains a first nucleotide sequence with a first segment coding, in 5' to 3' direction, for
(i) a 5' part of said RNA sequence of interest and
(ii) a 5' part of an intron; and said second vector contains a second nucleotide sequence with a second segment coding, in 5' to 3' direction, for
(i) a 3' part of an intron and
(ii) a 3' part of said RNA sequence of interest;

wherein said 5' part of the intron and said 3' part of the intron leads to the formation of said RNA sequence of interest by splicing of a primary transcript containing said 5' part of said RNA sequence of interest, said 5' part of the intron, said 3' part of the intron, and said 3' part of said RNA sequence of interest, thereby forming said RNA sequence of interest as a secondary transcript, wherein said primary transcript is transcribed from a functional transcription unit comprising said first nucleotide sequence and said second nucleotide sequence, and wherein said second vector is devoid of a transcriptional promoter for transcribing said 3' part of the intron and said 3' part of said RNA sequence of interest, and wherein (i) said first nucleotide sequence contains downstream of said first segment a recombination site for site-specific recombination, and (ii) said second nucleotide sequence contains upstream of said second segment a recombination site for site specific recombination, whereby said recombination sites are adapted for recombining with each other, optionally in the presence of a site-specific recombinase.

15. The process according to claim 14, wherein said first or said second nucleotide sequence contains a gene of a site-specific recombinase functional with said recombination sites.

16. The process according to claim 1, wherein three or more different vectors are provided to plant cells and wherein two or more different transgenic plant cells or plants are obtained, said different transgenic plant cells or plants expressing different RNA sequences of interest.

17. The process according to claim 1, wherein said first and said second nucleotide sequence are adapted such that said plants or said cells can be endowed with said trait of interest if and only if said plant cells are provided with said first vector and said second vector.

18. The process according to claim 1, wherein said RNA sequence of interest produces said trait of interest by causing degradation or suppression of a messenger RNA of said plant cells.

* * * * *

SEQUENCE LISTING

```
<160> NUMBER OF SEQ ID NOS: 8

<210> SEQ ID NO 1
<211> LENGTH: 44
<212> TYPE: DNA
<213> ORGANISM: Artificial Sequence
<220> FEATURE:
<223> OTHER INFORMATION: PCR primer

<400> SEQUENCE: 1
tttttggtcc gacctgcaac aataagaaca aaaagtcata aatt                          44

<210> SEQ ID NO 2
<211> LENGTH: 45
<212> TYPE: DNA
<213> ORGANISM: Artificial Sequence
<220> FEATURE:
<223> OTHER INFORMATION: PCR primer

<400> SEQUENCE: 2
tttaagcttg agctctttcc taggctcgaa gccgcggtgc gggtg                         45

<210> SEQ ID NO 3
<211> LENGTH: 53
<212> TYPE: DNA
<213> ORGANISM: Artificial Sequence
<220> FEATURE:
<223> OTHER INFORMATION: PCR primer

<400> SEQUENCE: 3
tttaagcttg aattcttttg gtctcaggta agtttcattt tcataattac aca                53

<210> SEQ ID NO 4
<211> LENGTH: 39
<212> TYPE: DNA
<213> ORGANISM: Artificial Sequence
<220> FEATURE:
<223> OTHER INFORMATION: PCR primer

<400> SEQUENCE: 4
tttttcaatt ggagctccta cgcccccaac tgagagaac                                39

<210> SEQ ID NO 5
<211> LENGTH: 20
<212> TYPE: DNA
<213> ORGANISM: Artificial Sequence
<220> FEATURE:
<223> OTHER INFORMATION: PCR primer

<400> SEQUENCE: 5
```

```
ccgtaccgag ccgcaggaac                                              20

<210> SEQ ID NO 6
<211> LENGTH: 23
<212> TYPE: DNA
<213> ORGANISM: Artificial Sequence
<220> FEATURE:
<223> OTHER INFORMATION: PCR primer

<400> SEQUENCE: 6
cagatctcgg tgacgggcag gac                                          23

<210> SEQ ID NO 7
<211> LENGTH: 22
<212> TYPE: DNA
<213> ORGANISM: Artificial Sequence
<220> FEATURE:
<223> OTHER INFORMATION: PCR primer

<400> SEQUENCE: 7
gaccgtgctt gtctcgatgt ag                                           22

<210> SEQ ID NO 8
<211> LENGTH: 21
<212> TYPE: DNA
<213> ORGANISM: Artificial Sequence
<220> FEATURE:
<223> OTHER INFORMATION: PCR primer

<400> SEQUENCE: 8
ggtttctggc agctggactt c                                            21
```